United States Patent
Belsham et al.

(10) Patent No.: US 11,299,735 B2
(45) Date of Patent: Apr. 12, 2022

(54) COMPOSITIONS AND METHODS FOR DETECTING AND TREATING INSULIN RESISTANCE

(71) Applicant: THE GOVERNING COUNCIL OF THE UNIVERSITY OF TORONTO, Toronto (CA)

(72) Inventors: Denise Belsham, Toronto (CA); Jennifer Chalmers, North York (CA)

(73) Assignee: The Governing Council of the University of Toronto, Toronto (CA)

( * ) Notice: Subject to any disclaimer, the term of this patent is extended or adjusted under 35 U.S.C. 154(b) by 0 days.

(21) Appl. No.: 16/475,549

(22) PCT Filed: Aug. 24, 2018

(86) PCT No.: PCT/CA2018/051020
§ 371 (c)(1),
(2) Date: Jul. 2, 2019

(87) PCT Pub. No.: WO2019/036811
PCT Pub. Date: Feb. 28, 2019

(65) Prior Publication Data
US 2020/0172902 A1    Jun. 4, 2020

Related U.S. Application Data

(60) Provisional application No. 62/697,935, filed on Jul. 13, 2018, provisional application No. 62/550,233, filed on Aug. 25, 2017.

(51) Int. Cl.
| | | |
|---|---|---|
| *C07H 21/04* | (2006.01) | |
| *C12N 15/113* | (2010.01) | |
| *A61P 3/10* | (2006.01) | |
| *A61K 9/00* | (2006.01) | |
| *A61K 9/08* | (2006.01) | |
| *C12Q 1/6883* | (2018.01) | |

(52) U.S. Cl.
CPC .......... *C12N 15/113* (2013.01); *A61K 9/0043* (2013.01); *A61K 9/08* (2013.01); *A61P 3/10* (2018.01); *C12Q 1/6883* (2013.01); *C12N 2310/113* (2013.01); *C12N 2310/141* (2013.01); *C12N 2310/315* (2013.01); *C12N 2310/3231* (2013.01); *C12N 2310/346* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2015/0337332 A1* 11/2015 Ruohoa-Baker ...... C12N 15/113
514/44 R

FOREIGN PATENT DOCUMENTS

| JP | 2015/223165 A | 12/2015 |
|---|---|---|
| WO | 2012/177639 A2 | 12/2012 |
| WO | 2014/096418 A2 | 6/2014 |

OTHER PUBLICATIONS

USPTO Published sequences 20150337332 mir1983 SEQ 4025.*
Mi, Huaiyu et al. Panther version 10: expanded protein families and functions, and analysis tools. Nucleic Acids Res. (2016), 44(D1):D336-42.
Miranda, Kevin C. et al. A Pattern-Based Method for the Identification of MicroRNA Binding Sites and Their Corresponding Heteroduplexes. Cell (2006), 126(6):1203-17.
Nazarians-Armavil, Anaies et al. Cellular insulin resistance disrupts hypothalamic mHypoA-POMC/GFP neuronal signaling pathways. J Endocrinol. (2013), 220(1):13-24.
Obici, Silvana et al. Decreasing hypothalamic insulin receptors causes hyperphagia and insulin resistance in rats. Nat Neurosci. (2002), 5(6):566-72.
Obici, Silvana et al. Hypothalamic insulin signaling is required for inhibition of glucose production. Nat Med. (2002), 8 (12):1376-82.
Parrizas, Marcelina and Novials, Anna. Circulating microRNAs as biomarkers for metabolic disease. Best Pract Res Clin Endocrinol Metab. (2016), 30(5):591-601.
Prentice, Kacey J et al. The Furan Fatty Acid Metabolite CMPF Is Elevated in Diabetes and Induces D Cell Dysfunction. Cell Metab. (2014), 19(4):653-66.
Rizza, R.A et al. Production of insulin resistance by hyperinsulinaemia in man. Diabetologia (1985), 28:70-75.
Roh, Eun et al. Emerging role of the brain in the homeostatic regulation of energy and glucose metabolism. Exp Mol Med. (2016), 48:e216.
Sangiao-Alvarellos, Susana. Perturbation of Hypothalamic MicroRNA Expression Patterns in Male Rats After Metabolic Distress: Impact of Obesity and Conditions of Negative Energy Balance. Endocrinology (2014), 155 (5):1838-50.
Scherer, Thomas et al. Brain Insulin Controls Adipose Tissue Lipolysis and Lipogenesis. Cell Metab. (2011), 13 (2):183-94.
Seeger, Timon et al. Long-Term Inhibition of miR-21 Leads to Reduction of Obesity in db/db Mice. Obesity (Silver Spring) (2014), 22(11):2352-60.
Thaler, Joshua P. et al. Obesity is associated with hypothalamic injury in rodents and humans. J Clin Invest. (2012), 122(1):153-62.
Trajkovski, Mirko et al. MicroRNAs 103 and 107 regulate insulin sensitivity. Nature (2011), 474(7353):649-53.
Turchinovitch, Andrey et al. Characterization of extracellular circulating microRNA. Nucleic Acids Res. (2011), 39(16):7223-33.
Valadi, Hadi et al. Exosome-mediated transfer of mRNAs and microRNAs is a novel mechanism of genetic exchange between cells. Nat Cell Biol. (2007), 9(6):654-9.

(Continued)

Primary Examiner — Kimberly Chong
(74) Attorney, Agent, or Firm — Bereskin & Parr LLP; Carmela De Luca; Amy Dam

(57) ABSTRACT

A miR-1983 inhibitor comprising an anti-miR-1983 oligonucleotide that is complementary to at least part of CTCACCTGGAGCATGTTTTCT (SEQ ID NO: 1), the part comprising at least nucleotides 2 to 8 of CTCACCTGGAGCATGTTTTCT (SEQ ID NO: 1).

Figure 1A:
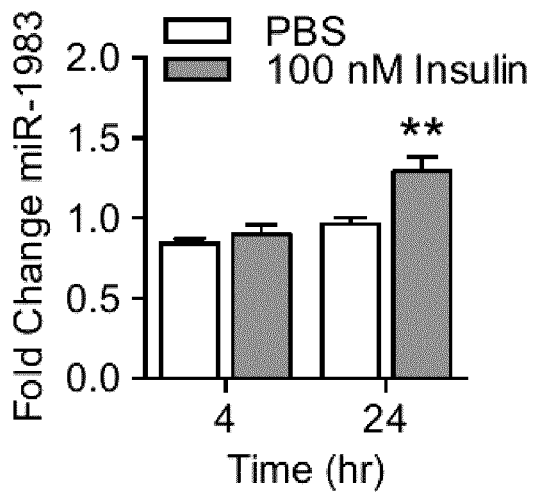
Figure 1A:
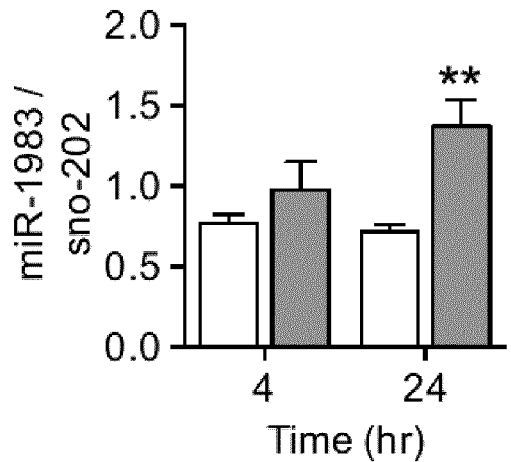
Figure 1B:
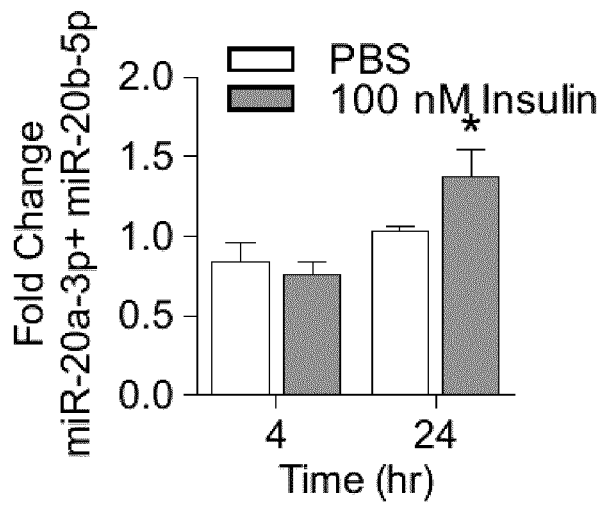
Figure 1B:
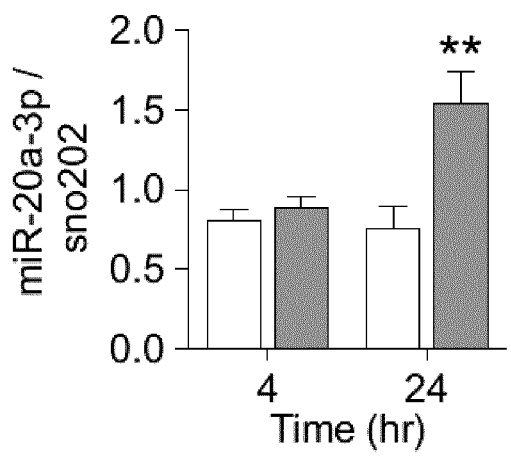
Figure 1C:
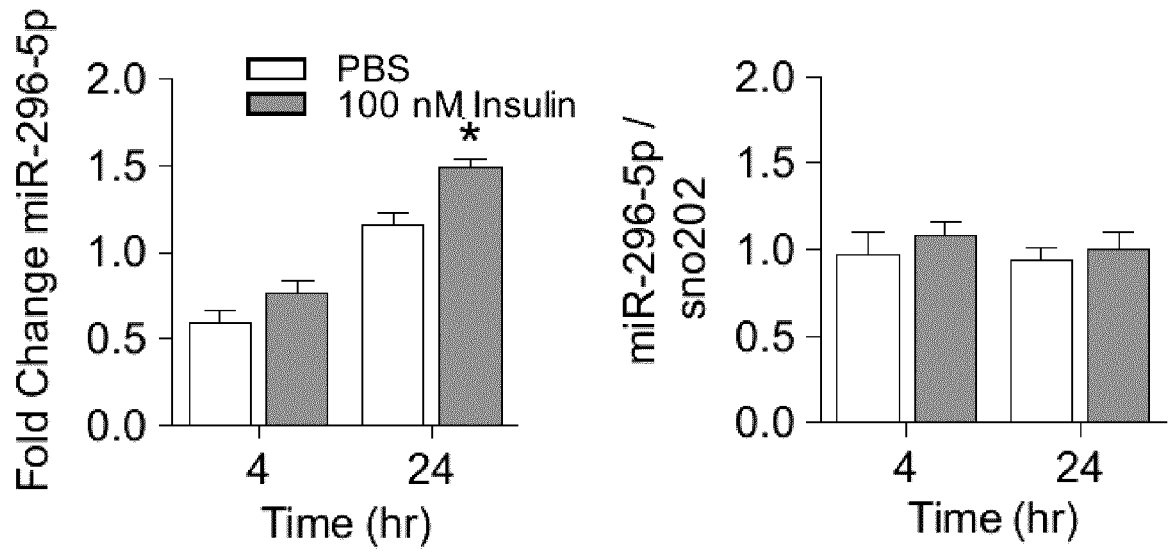

21 Claims, 16 Drawing Sheets
Specification includes a Sequence Listing.

(56) References Cited

OTHER PUBLICATIONS

Varela, Luis and Horvath, Tamas L. Leptin and insulin pathways in POMC and AgRP neurons that modulate energy balance and glucose homeostasis. EMBO Rep. (2012), 13(12):1079-86.
Vienberg, S. et al. MicroRNAs in metabolism. Acta Physiol (Oxf). (2017), 219(2):346-361.
Vinnikov, Ilya A. et al. Hypothalamic miR-103 Protects from Hyperphagic Obesity in Mice. J Neurosci. (2014), 34 (32):10659-74.
Wellhauser, Leigh et al. Nitric Oxide Exerts Basal and Insulin-Dependent Anorexigenic Actions in POMC Hypothalamic Neurons. Mol Endocrinol. (2016), 30(4):402-16.
Mi, Huaiyu et al. Large-scale gene function analysis with the PANTHER classification system. Nature Protocold, vol. 8, No. 8, p. 1551-1566, Jul. 8, 2013.
Meredith, M. Elizabeth et al. Intranasal Delivery of Proteins and Peptides in the Treatment of Neurodegenerative Diseases. The AAPS Journal, vol. 17, No. 4, Jul. 2015.
Meister, Björn et al. MicroRNAs in the Hypothalamus. Neuroendocrinology. Sep. 2013, 98:243-253.
Medrikova, D. et al. Sex differences during the course of diet-induced obesity in mice: adipose tissue expandability and glycemic control. International Journal of Obesity (2012) 36, 262-272.
Mayer, Christopher M. et al. Palmitate Attenuates Insulin Signaling and Induces Endoplasmic Reticulum Stress and Apoptosis in Hypothalamic Neurons: Rescue of Resistance and Apoptosis through Adenosine 5' Monophosphate-Activated Protein Kinase Activation. Endocrinology, Feb. 2010, 151(2):576-585.
Mayer, Christopher M. et al. Central Insulin Signaling Is Attenuated by Long-Term Insulin Exposure via Insulin Receptor Substrate-1 Serine Phosphorylation, Proteasomal Degradation, and Lysosomal Insulin Receptor Degradation. Endocrinology, Jan. 2010, 151(1):75-84.
Loh, Kim et al. Insulin controls food intake and energy balance via NPY neurons. Molecular Metabolism 6 (2017) 574-584.
Mayer, Christopher M. et al. Insulin directly regulates NPY and AgRP gene expression via the MAPK MEK/ERK signal transduction pathway in mHypoE-46 hypothalamic neurons. Molecular and Cellular Endocrinology 307 (2009) 99-108.
Livak, Kenneth J. et al. Analysis of Relative Gene Expression Data Using Real-Time Quantitative PCR and the 2CT Method. Methods 25, 402-408 (2001).
Liu, Ying et al. Rapid Elevation in CMPF May Act as a Tipping Point in Diabetes Development. Cell Reports 14, 2889-2900 (Mar. 29, 2016).
Liu, Jidong et al. MicroRNA-dependent localization of targeted mRNAs to mammalian P-bodies. Nat Cell Biol. Jul. 2005 ; 7(7): 719-723.
Li, Yu et al. Method for microRNA isolation from clinical serum samples. Analytical Biochemistry 431 (2012) 69-75.
Lewis, Benjamin P. et al. Conserved Seed Pairing, Often Flanked by Adenosines, Indicates that Thousands of Human Genes are MicroRNA Targers. Letter to th Editor. Cell, vol. 120, 15-20, Jan. 14, 2005.
Levy, Jonathan C. Correct Homeostasis Model Assessment (HOMA) Evaluation Uses the Computer Program. Diabetes Care, vol. 21. No. 12, p. 2191-2192, Dec. 1998.
Lee, Soom-Tae et al. miR-206 Regulates Brain-Derived Neurotrophic Factor in Alzheimer Disease Model. Ann Neurol 2012;72:269-277.
Lee, Alex K. et al. Effect of high-fat feeding on expression of genes controlling availability of dopamine in mouse hypothalamus. Nutrition 26 (2010) 411-422.
Kuehnert, Julia et al. Novel RNA chaperone domain of RNA-binding protein La is regulated by AKT phosphorylation. Nucleic Acids Research, 2015, vol. 43, No. 1 581-594.
Kornfeld, Jam-Wilhelm et al. Obesity-induced overexpression of miR-802 impairs glucose metabolism through silencing of Hnf1b. Feb. 7, 2013, Nature, Vo. 494, 111-115.
Könner, A. Christine et al. Selective Insulin and Leptin Resistance in Metabolic Disorders. Cell Metabolism 16, Aug. 8, 2012, 144-152.
Kleinridders, Andé et al. Insulin Action in Brain Regulates Systemic Metabolism and Brain Function. Diabetes 2014;63:2232-2243.
Kim, Jeong-Min et al. Inhibition of Let7c MicroRNA Is Neuroprotective in a Rat Intracerebral Hemorrhage Model. PLOS One, Jun. 2014, vol. 9, Issue 6.
Kaushik, Susmita et al. Loss of autophagy in hypothalamic POMC neurons impairs lipolysis. EMBO reports, vol. 13, No. 3 (2012).
Janssen, Harry L.A. et al. Treatment of HCV Infection by Targeting MicroRNA. The New England Journal of Medicine, 368;18 nejm.org May 2, 2013.
Hollander, Jonathan A. et al. Striatal microRNA controls cocaine intake through CREB signalling. Nature, vol. 466, Jul. 8, 2010.
Herzer, S. et al. Locked Nucleic Acid-Based In Situ Hybridisation Reveals miR-7a as a Hypothalamus-Enriched MicroRNA with a Distinct Expression Pattern. Journal of Neuroendocrinology 2012, 24, 1492-1504.
Hasler, Daniele et al. The Lupus Autoantigen La Prevents Mischanneling of tRNA Fragments into the Human MicroRNA Pathway. Molecular Cell 63, 110-124 (2016).
Hashimoto, Naoko et al. Role of miRNAs in the pathogenesis and susceptibility of diabetes mellitus. Journal of Human Genetics (2017) 62, 141-150.
Gao, Qian et al. Neuronal control of energy homeostasis. FEBS Letters 582 (2008) 132-141.
Feng, Juan et al. Regulatory Roles of MicroRNAs in Diabetes. Int. J. Mol. Sci. 2016, 17, 1729.
Edinger, Robert S. Aldosterone Regulates MicroRNAs in the Cortical Collecting Duct to Alter Sodium Transport. J Am Soc Nephrol 25: 2445-2457, 2014.
Elmasry, K. et al. Epigenetic modifications in hyperhomocysteinemia: potential role in diabetic retinopathy and age-related macular degeneration. Oncotarget, Jan. 29, 2018, vol. 9(16), pp. 12562-12590.
Ching-Hua, Hsieh et al. Weight-reduction through a low-fat diet causes differential expression of circulating microRNAs in obese C57BL/6 mice. BMC Genomics (2015), 16:699.
Agarwal, Vikram et al. Predicting effective microRNA target sites in mammalian mRNAs. eLife 4, e05005 (2015).
Arroyo, Jason D. et al. Argonaute2 complexes carry a population of circulating microRNAs independent of vesicles in human plasma. PNAS (2011), 108(12):5003-8.
Balcells, Ingrid et al. Specific and sensitive quantitative RT-PCR of miRNAs with DNA primers. BMC Biotechnology (2011), 11:70.
Belgardt, Bengt F. et al. Hormone and glucose signalling in POMC and AgRP neurons. J Physiol (2009), 587(Pt 22):5305-14.
Belsham, Denise D. et al. Generation of a Phenotypic Array of Hypothalamic Neuronal Cell Models to Study Complex Neuroendocrine Disorders. Endocrinology (2004), 145(1): 393-400.
Bergen, Hugo T. et al. Resistance to diet-induced obesity is associated with increased proopiomelanocortin mRNA and decreased neuropeptide Y mRNA in the hypothalamus. Brain Research (1999), 851(1-2):198-203.
Betel, Doron et al. Comprehensive modeling of microRNA targets predicts functional non-conserved and non-canonical sites. Genome Biology (2010), 11(8):R90.
Betel, Doron et al. The microRNA.org resource: targets and expression. Nucleic Acids Research (2008), 36 (Database issue):D149-53.
Bhattacharyya, Suvendra N. et al. Relief of microRNA-Mediated Translational Repression in Human Cells Subjected to Stress. Cell (2006), 125:1111-1124.
Born, Jan et al. Sniffing neuropeptides: a transnasal approach to the human brain. Nat Neurosci. (2002), 5(6):514-6.
Bruning, Jens C. et al. Role of Brain Insulin Receptor in Control of Body Weight and Reproduction. Science (2000), 289(5487): 2122-5.
Clegg, Deborah J. et al. Consumption of a high-fat diet induces central insulin resistance independent of adiposity. Physiology & Behavior (2011), 103(1): 10-6.
Crepin, Delphine et al. The over-expression of miR-200a in the hypothalamus of ob/ob mice is linked to leptin and insulin signaling impairment. Molecular and Cellular Endocrinology (2014), 384(1-2): 1-11.

(56) References Cited

OTHER PUBLICATIONS

Dhillon, Sandeep S. et al. Cellular Leptin Resistance Impairs the Leptin-Mediated Suppression of Neuropeptide Y Secretion in Hypothalamic Neurons. Endocrinology (2011), 152(11):4138-47.
Dhuria, Shyeilla V. et al. Intranasal Delivery to the Central Nervous System: Mechanisms and Experimental Considerations. J. Pharm. Sci. (2010), 99(4): 1654-73.
Dweep, H. and Gretz, N. miRWalk2.0: a comprehensive atlas of microRNA-target interactions. Nat Methods. (2015), 12(8):697.
Dweep, Harsh et al. miRWalk—Database: Prediction of possible miRNA binding sites by "walking" the genes of three genomes. Journal of Biomedical Informatics 44 (2011) 839-847.
Torres A. G. et al. MicroRNA fate upon targeting with anti-miRNA oligonucleotides as revealed by an improved Northern-blot-based method form miRNA detection. RNA, vol. 17, No. 5, Mar. 25, 2011, pp. 933-943.
Matthaei S. et al. Pathophysiology and pharmacological treatment of insuline resistance. Endocrine Reviews, vol. 21, No. 6, Dec. 1, 2000, pp. 585-618.

* cited by examiner

COMPOSITIONS AND METHODS FOR DETECTING AND TREATING INSULIN RESISTANCE

RELATED APPLICATIONS

This application is a national phase entry of PCT/CA2018/051020, filed Aug. 24, 2018, which claims priority from U.S. Provisional patent applications serial numbers 62/550,233 filed Aug. 25, 2017, and 62/697,935 filed Jul. 13, 2018; each of these applications being incorporated herein in their entirety by reference.

INCORPORATION OF SEQUENCE LISTING

A computer readable form of the Sequence Listing "P53603US02_Sequence_Listing.txt" (9,798 bytes), submitted via EFS-WEB and created on Jun. 28, 2019, is herein incorporated by reference.

FIELD

This disclosure relates to a miRNA related to insulin resistance and the use of its antagonist as a therapeutic.

BACKGROUND

The hypothalamus functions as the key modulator of nutritional status and energy homeostasis in the body. The neuropeptide Y (NPY)/agouti-regulated peptide (AgRP)- and pro-opiomelanocortin (POMC)-expressing neurons that coordinate food intake and energy expenditure are crucial in maintaining energy homeostasis. Located in the arcuate nucleus (ARC) (Gao and Horvath, 2008; Varela and Horvath, 2012), situated close to the third ventricle, and projecting to the median eminence, these NPY neurons, co-expressing agouti-related peptide (AgRP), and POMC neurons are ideally localized to sense changes in circulating factors such as peripheral hormones and dietary components. This information is relayed to other nuclei of the hypothalamus and further brain regions to maintain a healthy energy balance. Functional disruptions of the NPY/AgRP or POMC neuronal populations, in particular those that alter their response to peripheral signals such as insulin and leptin, have been linked to obesity, insulin resistance, and development of type II diabetes mellitus (T2DM) (Konner and Bruning, 2012; Roh et al., 2016). It has also been determined that weight-reduction through a low-fat diet causes differential expression of circulating microRNAs in obese mice (Hsieh et al., 2015).

Insulin resistance is fairly well-defined in peripheral tissues, but the underlying pathology has been less characterized in the brain (Kleinridders et al., 2014). Studies of brain insulin signaling in rodent models have been fruitful in determining the critical role of insulin signaling in the prevention of diet-induced obesity, dysregulation of hepatic glucose production in response to high fat intake, as well as maintaining normal white adipose tissue lipogenesis and lipolysis, which is disturbed in T2DM (Bruning et al., 2000; Obici et al., 2002b; Scherer et al., 2011). Further supporting the importance of the brain in the development of metabolic dysregulation, Clegg et al. established that insulin resistance occurs in the brain prior to peripheral tissues, and precedes the development of adiposity on a high fat diet (HFD) (Clegg et al., 2011). In fact, even a partial decrease in insulin receptor (InsR) levels in NPY/AgRP neurons of the ARC alone is sufficient to induce insulin resistance and hyperphagia in rats (Obici et al., 2002a). While most recently, insulin signaling specifically in NPY neurons was found to be crucial for the control of food intake and energy balance (Loh et al., 2017). Thus, impairment of central insulin signaling potentially acts as a precipitating factor for the development of peripheral insulin resistance, however the mechanisms by which this pathology occurs remain understudied.

Hyperinsulinemia, which can trigger insulin resistance, can also occur independently of obesity (Rizza et al., 1985). For example, it has a been demonstrated that an NPY/AgRP neuronal cell model exposed to high levels of insulin become insulin resistant between 8-24 h (Mayer and Belsham, 2010a). Decreased protein levels of InsR and InsR substrate-1 (IRS-1), but not their mRNA levels, were credited for the abolished cellular signaling observed. The proteosomal and lysosomal pathways were linked to IRS-1 and InsR degradation, respectively, upon prolonged insulin exposure. Similarly, POMC expressing neuronal cell models were also found to develop insulin resistance with this paradigm (Nazarians-Armavil et al., 2014). These experiments elucidated the means by which key proteins in the insulin signaling pathway could be degraded upon high insulin exposure in hypothalamic cells.

SUMMARY

According to an aspect of the invention there is provided a miR-1983 inhibitor comprising an anti-miR-1983 oligonucleotide that is complementary to at least part of CTCACCTGGAGCATGTTTTCT (SEQ ID NO: 1), the part comprising at least nucleotides 2 to 8 of CTCACCTGGAGCATGTTTTCT (SEQ ID NO: 1).

In an embodiment, the mIR-1983 inhibitor is the anti-miR-1983 oligonucleotide.

According to another aspect of the invention there is a composition comprising the miR-1983inhibitor and a diluent.

According to yet a further aspect, there is a method of detecting if a cell is insulin resistant comprising measuring the level of miR-1983 and comparing to a threshold or control, wherein an increased level compared to the control is indicative the cell is insulin resistant.

According to another aspect there is a method of detecting pre-diabetes or an increased likelihood of developing diabetes in a subject, the method comprising measuring a level of miR-1983 in a biological sample from the subject, wherein an increased level compared to a threshold or control is indicative that the subject has pre-diabetes or an increased likelihood of developing diabetes.

According to another aspect there is a method of improving insulin sensitivity in a subject, the method comprising administering an miR-1983 inhibitor to a subject in need thereof.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

DRAWINGS

Embodiments are described below in relation to the drawings in which:

FIG. 1 depicts a microarray (n=3) and qPCR validation (n=4-5) of miRNAs found to be altered in the mHypoE-46 cell line upon the induction of insulin resistance. FIG. 1A depicts miR-1983, FIG. 1B depicts miR-20a-3p, FIG. 1C depicts miR-296-5p, and FIG. 1D depicts Let-7d-5p. *p<0.05, ** p<0.01.

Figure 2A:
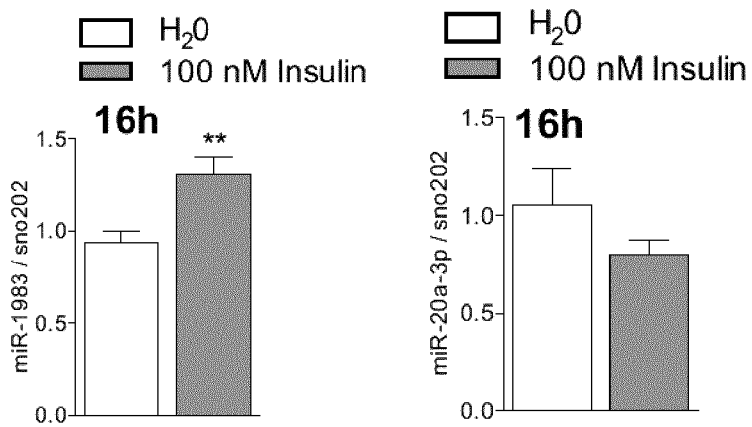
Figure 2B:
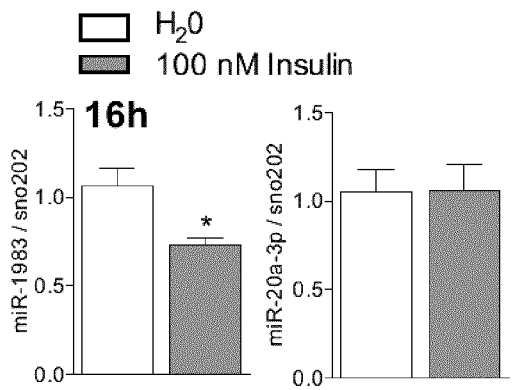
Figure 2C:
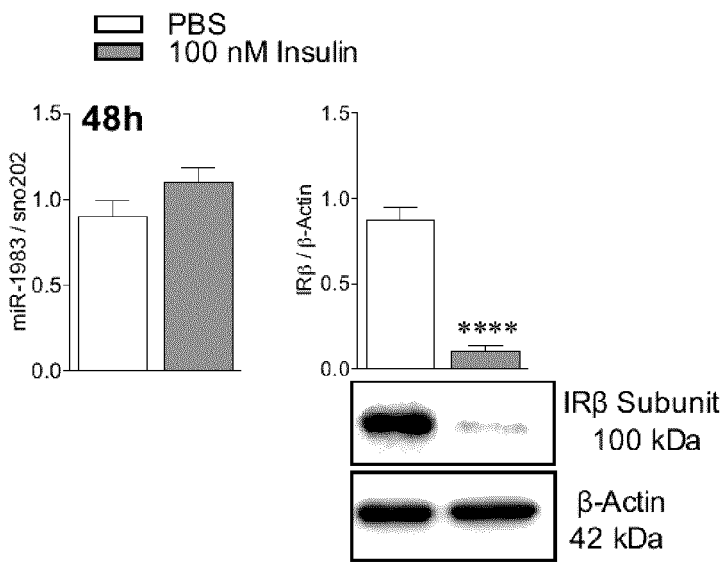

FIG. 2 shows that miR-1983 is regulated in adult cell lines and is not permanently upregulated upon insulin treatment. Insulin resistance induces differential changes in miR-1983, but not miR-20a-3p in both adult FIG. 2A female mHypoA-NPY/GFP (n=3-7) and FIG. 2B male mHypoA-POMC/GFP-2 (n=8-16) cell lines. FIG. 2C miR-1983 upregulation in the mHypoE-46 cells is absent 48 hours after while the loss of InsRβ-subunit protein levels persists (n=8). Data shown are mean±s.e.m. *P<0.05, P<0.01, **P<0.0001.

FIG. 3 depicts in silica and in vitro analysis of mRNA targets of miR-1983. FIG. 3A shows in silica analysis workflow schematic to assess miR-1983 gene targets of interest and FIG. 3B is a targetscan analysis of the insulin receptor (Insr) 3' untranslated region (3'UTR) in mouse (above) and conserved cross-species alignment of the Insr 3'UTR sequence target region for miR-1983 (below). Predicted consequential pairing of a portion of the Ins 3' UTR target region (SEQ ID NO: 38) and a miRNA (SEQ ID NO: 39) is shown. FIG. 3C shows mRNA levels of Insr are unaltered after transfection of a miR-1983 miRNA mimic (25 nM) into mHypoE-46 cells for 24 hours (n=4). FIG. 3D InsRβ. protein levels are decreased after transfection of a miR-1983 miRNA mimic (25 nM) into mHypoE-46 cells for 24 hours (n=4). FIG. 3E mRNA levels of Insr after transfection of a miR-1983 miRNA mimic (25 nM) into mHypoE-46 cells for 48 hours (n=4) are unaltered, while InsR[3. protein levels are decreased after transfection of a miR-1983 miRNA mimic (25 nM) into mHypoE-46 cells for 48 hours (n=4). FIG. 3F Transfection of the pmirGLO vector (1 µg) containing ~3000 bp 3'Insr-UTR sequence concurrently with the miR-1983 mimic (25 nM) (n=3-4 independent experiments/group, each run in triplicate).* Data shown are mean±s.e.m. P<0.05, ** P<0.01.

FIG. 4 shows that miR-1983 is upregulated in the hypothalamus of male but not female C57BL/6 mice fed a HFD for 7-9 weeks, despite displaying similar changes in neuropeptide mRNA levels. Male and female C57BL/6 mice fed a 60% HFD compared to a sucrose-matched control diet (Chow) for 7-9 weeks have increased body weight (FIG. 4A, n=4-7/group) and fasting blood glucose (FIG. 4B, n=3-7/group), and display similar changes in Npy, AgRP, and Insr, but not Pomc expression (FIGS. 4C & D, n=7-8/group). Only male C57BL/6 display an increase in fasting insulin and hypothalamic miR-1983 levels (FIGS. 4E & F, n=7-8/group), *p<0.05, p<0.01, **p<0.0001. Data shown are mean±s.e.m.

FIG. 5 shows that miR-1983 is upregulated in the hypothalamus of male CD-1 mice on a HFD after 5, but not 10 weeks, preceding complete alterations in neuropeptide mRNA levels. Compared to a sucrose-matched control diet, mice fed 60% HFD for 5 weeks have increased circulating fasting blood glucose (FIG. 5A, n=4/group), and insulin levels (FIG. 5B, n=8/group). The expression of miR-1983 was increased in the hypothalamus of these mice (FIG. 5C, n=9-12), with no alterations in Npy, AgRP, Pomc, or Insr mRNA levels (FIG. 5D, n=8-14/group). CD-1 mice fed the same diets for 10 weeks did not have increased levels of hypothalamic miR-1983 (FIG. 5E, n=10-11/group), but exhibited decreases in Npy and AgRP in mRNA and an increase in Pomc mRNA. No change Insr mRNA abundance was detected (FIG. 5F, n=8-11/group). Data shown are mean±s.e.m, *p<0.05, p<0.01, *p<0.001.

FIG. 6 shows that miR-1983 is not elevated in the hypothalamus of CD-1 female mice fed for 5 weeks on a 60% HFD, while male mice display upregulation in their hypothalamus and serum with decreased levels in the kidney. Both sexes have increased body weight gain for both control and 60% HFD groups (FIGS. 6A & B, n=8-9/group) and total body weight (FIG. 6C, n=8-9/group) relative to their littermates fed chow. 4 hour fasting blood glucose (n=7-9/group) for male and female CD-1 mice fed either chow (sucrose-matched control diet) or 60% HFD (FIG. 6D, n=7-9/group). (FIG. 6E) Hypothalamic miR-1983 and fasting insulin levels of male CD-1 mice on chow (n=7-8), or 60% HFD(n=8) compared to MKR (n=8) mice. Both male (FIG. 6F) Hypothalamic miR-1983 and fasting insulin levels of female CD-1 mice on chow (n=7-8), or 60% HFD (n=8) compared to MKR (n=3) mice. Male (FIG. 6G, n=7-9/group) and female (FIG. 6H, n=8-9/group) mice displayed a lower level of Npy mRNA, without changes in AgRP or Pomc mRNA quantities; however, Insr mRNA levels were increased in female mice only. (FIG. 6I) miR-1983 levels in male CD-1 mice in the muscle, kidney, and serum (n=5-8/group) on chow versus a 60% HFD. Data shown are mean±s.e.m, *p<0.05, p<0.01, **p<0.0001.

FIG. 7 shows that in vivo intranasal delivery of miR-1983 inhibitor or control in CD-1 mice over a 5 week 60% HFD regiment, induces changes in insulin sensitivity, fasting blood glucose, and hypothalamic InsRβ-subunit protein levels. (FIG. 7A) Experimental paradigm (time line) of in vivo miR-1983 inhibitor administration to mice on a 60% HFD. These animals displayed an increase in body weight gain (FIG. 7B, n=5-6/group) and total body weight (FIG. 7C, n=5-6/group) compared to chow (sucrose-matched control diet). (FIG. 7D) Intraperitoneal insulin tolerance test (IpITT), (4 h fast plus 1 unit of insulin/kg body weight) (n=5-6/group). (FIG. 7E) Fasting blood glucose levels after two weeks post intranasal administration of miR-1983 inhibitor (n=5-6/group). (FIG. 7F) Neuropeptides Hypothalamic Npy, Agrp, Pomc and Insr mRNA levels were decreased similarly in both 60% HFD groups after 5 weeks. (FIG. 7G) InsRβ-subunit protein subunit was decreased in the mice on a 60% HFD but not in the miR-1983 inhibitor group at the conclusion of the 5 week study (n=5-6/group). Data shown are mean±s.e.m, *p<0.05, p<0.01, *p<0.001, ****p<0.0001.

Figure 8:
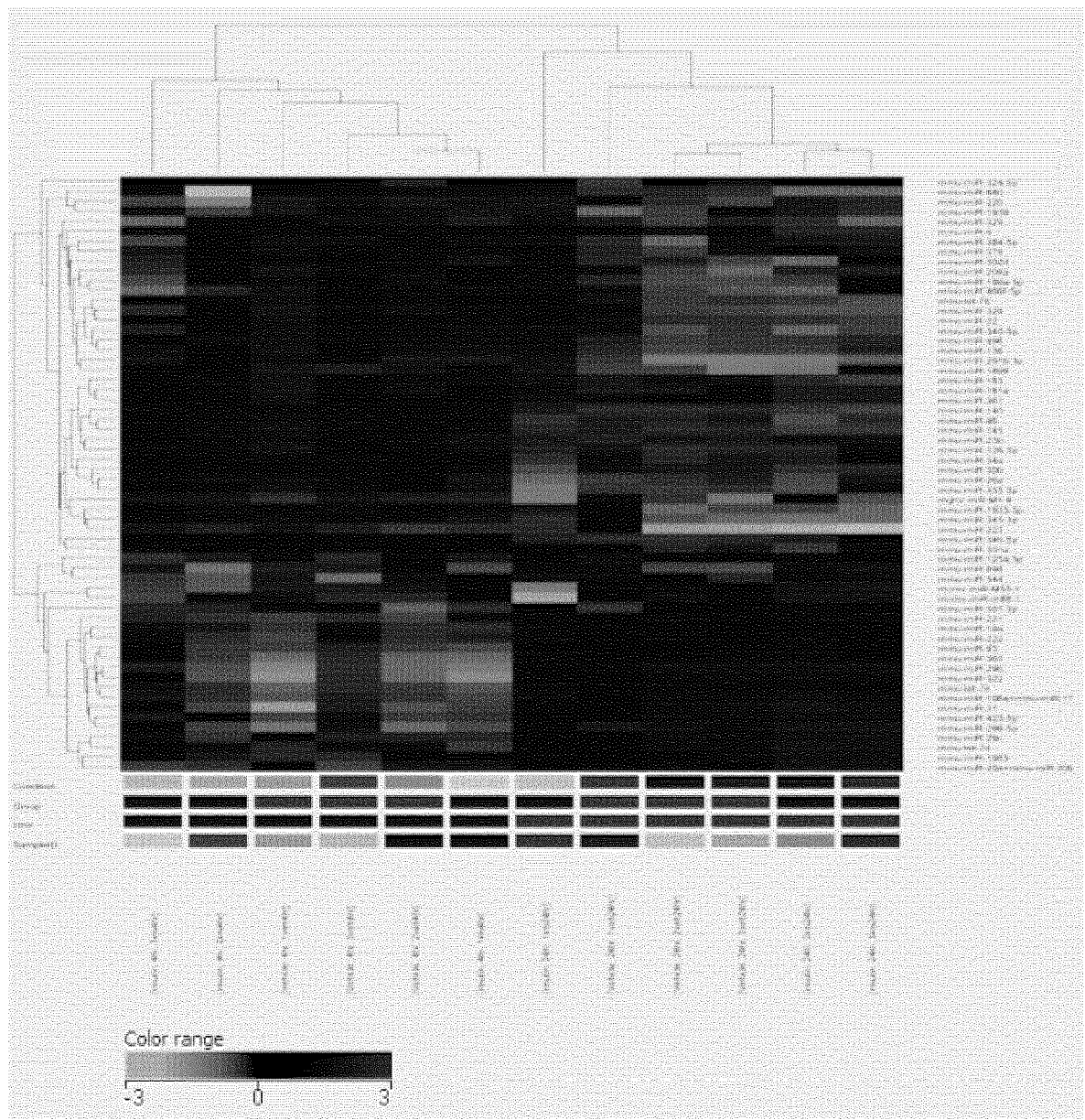

FIG. 8 depicts a microarray heat map of 60 miRNAs that changed upon 100 nM insulin treatment in the mHypoE-46 cell line.

Figure 9:
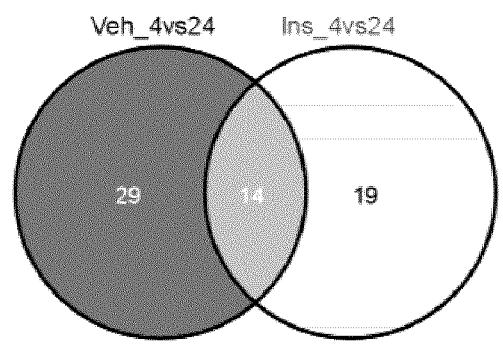

FIG. 9 depicts Venn diagram illustration of the 60 miRNAs altered across all treatment groups for 4 versus 24 hours. Vehicle PBS treatment (Veh) and 100 nM insulin treatment (Ins).

Figure 10B:
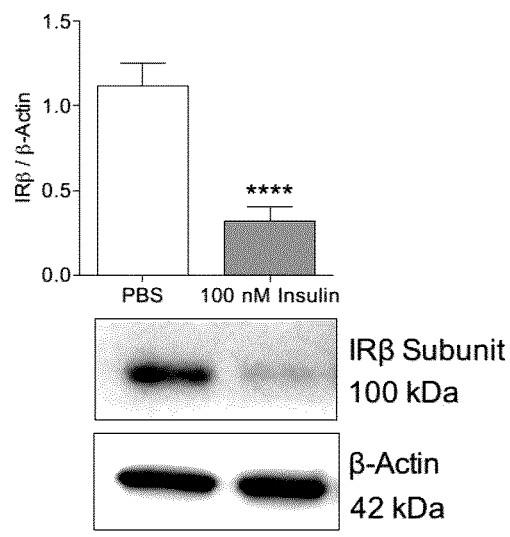
Figure 10A:
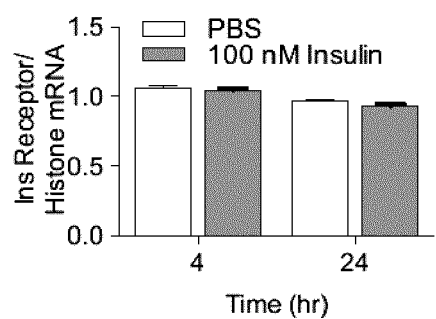

FIG. 10 depicts validation data illustrating that the mRNA levels of the InsR remain unaltered in mHypoE-46 cells treated with 100 nM of insulin for 4 or 24 hours (FIG. 10A, n=5). This cell model exhibited a decrease in InsRβ-subunit protein levels characteristic of insulin resistance (FIG. 10B, n=10). Data shown are mean±s.e.m. ****P<0.0001.

FIG. 11 shows that serum miR-1983 levels are correlated with circulating insulin levels in male mice and in both male and female human subjects. (FIG. 11A) Total body weight (n=8-9/group) for male and female CD-1 mice fed either chow (sucrose-matched control diet) or 60% HFD. (FIG.

11B) Correlation of serum miR-1983 levels with glucose (left) and insulin (right) in male CD-1 mice fed a chow or 60% HFD. (FIG. 11C) Serum levels of miR-1983 in humans separated by body mass index for <25 (n=2, SD shown as 5 subjects had no detectable levels of miR-1983), 25-29.9 (n=8), >30 (n=9). (FIG. 11D) Correlation analysis of serum miR-1983 levels with various blood parameters (solid circles are statistically significant, see Table 1 for full analysis details). (FIG. 11E) Linear regression analysis of serum insulin (left) and homeostatic model assessment-insulin resistance (HOMA-IR) (right) scores with serum miR-1983 levels in humans Data shown are mean±s.e.m unless otherwise indicated. *P<0.05, P<0.01, *P<0.001, ****P<0.0001.

DESCRIPTION OF VARIOUS EMBODIMENTS

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. For example, the term "a cell" includes a single cell as well as a plurality or population of cells. Generally, nomenclatures utilized in connection with, and techniques of, cell and tissue culture, molecular biology, and protein and oligonucleotide or polynucleotide chemistry and hybridization described herein are those well-known and commonly used in the art (see, e.g. Green and Sambrook, 2012).

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 20%, 5-20%, or 10-20%, preferably 5-15%, more preferably 5% or 10%, of the number to which reference is being made.

The term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

Further, the definitions and embodiments described in particular sections are intended to be applicable to other embodiments herein described for which they are suitable as would be understood by a person skilled in the art. For example, in the following passages, different aspects of the disclosure are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Terms of degree such as "about", "substantially", and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "nucleic acid" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acids of the present disclosure may be deoxyribonucleic acid sequences (DNA) or ribonucleic acid sequences (RNA) and may include naturally occurring bases including adenine, guanine, cytosine, thymidine and uracil. The sequences may also contain modified bases, for example to provide increase to nuclease resistance. The nucleic acid can be either double stranded or single stranded, and represents the sense or antisense strand. Further, the term "nucleic acid" includes the complementary nucleic acid sequences as well as codon optimized or synonymous codon equivalents. The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived. The term "nucleic acid" can also include, for example, "antisense nucleic acids," "antisense oligonucleotides", "miRNA", anti-miRNA and the like.

The term "oligonucleotide" as used herein refers to a short nucleic acid comprising, a sequence of nucleotide or nucleoside monomers consisting of naturally and non-naturally occurring bases, sugars, and intersugar (backbone) linkages, and includes single-stranded and double-stranded molecules, RNA and DNA. Typically, oligonucleotides are less than 50 monomers, including non-naturally occurring monomers, more typically, 30 monomers or less. The term "oligonucleotide" includes, for example, "antisense oligonucleotides" and "miRNA" as well as oligonucleotide analogues such as "morpholino oligonucleotides", "phosphorothioate oligonucleotides."

The term "chemically modified oligonucleotide" as used herein refers to an oligonucleotide comprising at least one non-naturally occurring monomer (e.g. a modified monomer). Such chemically modified oligonucleotides can have similar or better binding capabilities as non-modified oligonucleotides. Similar as used in this context means that the chemically modified oligonucleotide binds its target with a binding specific that is within 20% of a polynucleotide lacking the particular modification. The chemical modification can be one found in locked nucleic acids (LNAs) or can be 2'-fluoro (2'-F), 2'-O-methoxyethyl (2'-MOE) or 2'-O-methyl (2'-O-Me), which are modifications at the 2' position of the ribose moiety or morpholino monomer where a six-membered morpholine ring replaces the sugar moiety or phosphorothioate (PS) linkage where sulfur replaces one of the non-bridging oxygen atoms in the phosphate group. The non-naturally occurring monomer can comprise one or more chemical modifications. For example, phosphorothioate linkages can also be incorporated into any of the above mentioned chemically modified oligonucleotides. Such modified or substituted nucleic acids may be preferred over naturally occurring forms because of properties such as increased stability in the presence of nucleases. The term also includes chimeric nucleic acids that contain two or more chemically distinct regions. For example, chimeric nucleic acids may contain at least one region of modified nucleotides that confer beneficial properties (e.g., increased nuclease resistance, increased uptake into cells), or two or regions of modified nucleotides.

An "antisense nucleic acid" or "antisense oligonucleotide" comprises a nucleotide sequence, which is complementary to a "sense" nucleic acid e.g., complementary to miR-1983. Accordingly, an antisense nucleic acid can hydrogen bond to a sense nucleic acid. For example, the nucleic acid can comprise DNA, RNA or a chemical analog (e.g. comprising one or more modified monomers) that binds to the target DNA or RNA. Antisense nucleic acid molecules may be chemically synthesized using naturally occurring nucleotides or variously modified nucleotides designed to increase the biological stability of the molecules or to increase the physical stability of the duplex formed with the target RNA or DNA e.g., phosphorothioate derivatives and acridine substituted nucleotides. The antisense nucleic acid can be complementary to an entire target strand, or only to a portion thereof. As is known in the art, antisense sequences can be produced using a variety of methods. The antisense sequences can be produced biologically using an expression vector introduced into cells in the form of a recombinant plasmid, phagemid or attenuated virus in which antisense sequences are produced under the control of a high-efficiency regulatory region, the activity of which may be determined by the cell type into which the vector is introduced. Additionally, antisense sequences can be purchased from manufacturers.

The term "anti-miR-1983 oligonucleotide" as used herein refers to an antisense oligonucleotide which is at least 7 nucleotides long and is complementary to at least nucleotides 2 to 8 of the sequence 5'-3', CTCACCTGGAG-CATGTTTTCT (SEQ ID NO: 1). Anti-miR-1983 can be for example composed of DNA, RNA, or LNA monomers or other modified bases or a combination of any of thereof.

The term "coding region" refers to the region of the nucleotide sequence comprising codons, which are translated into amino acid residues.

The term "noncoding region" of a gene or cDNA refers to 5' and 3' sequences, which flank the coding region that are not translated into amino acids (i.e., also referred to as 5' and 3' untranslated regions).

The term "morpholino monomer" refers to a subunit comprising a nucleic acid base, a 6 membered morpholine ring and a non-ionic phosphorodiamidate intersubunit linkage. Morpholino oligonucleotides are short chains of about 25 morpholino subunits. Each Morpholinos block small (~25 base) regions of the base-pairing surfaces of ribonucleic acid (RNA).

The term "a cell" as used herein includes a plurality of cells and includes a cell line.

The term "cell line" as used herein refers to a group of genetically uniform immortal cells that be propagated in vitro for an indefinite term. The cell line can derive from a single clone (e.g., monoclonal cell line) or from more than one clone (e.g., polyclonal cell line).

The term "a biological sample" as used herein refers to a sample of fluid or tissue sample derived from a subject. Examples of fluid samples include, but are not limited to, blood, plasma, serum, urine, spinal fluid, lymph fluid, tears, saliva, sputum and milk. An example of a tissue sample includes a brain tissue sample or a nerve tissue sample. Methods of obtaining such biological samples are known in the art including but not limited to standard blood retrieval procedures.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, such as slowing or reversing progression to insulin resistance, substantially ameliorating clinical or aesthetical symptoms of a condition such as improving insulin sensitivity or substantially preventing the appearance of clinical or aesthetical symptoms of a condition.

As used herein, the term "administration" means to provide or give a subject an agent, such as a composition comprising an effective amount of a miR-1983 inhibitor by an effective route such as an intranasal administration route.

As used herein, the term "effective amount" refers to an amount of an agent, such as an miR-1983 inhibitor that is sufficient to generate a desired response, such as reduce or eliminate a sign or symptom of a condition. In some examples, an "effective amount" is one that treats (including prophylaxis) one or more symptoms and/or underlying causes of any of a disorder or disease. An effective amount may be a therapeutically effective amount, including an amount that prevents one or more signs or symptoms of a particular disease or condition from developing, such as one or more signs or symptoms associated with insulin resistance or pre-diabetes.

As used herein, the term "complementarity" means the nucleobase pairing ability between a first nucleic acid and a second nucleic acid.

As used herein, the term "insulin sensitivity" refers to the physiological condition in which cells respond to the normal actions of the hormone insulin. This is in contrast to insulin resistance, which is a physiological condition in which cells fail to respond to the normal actions of insulin. Accordingly, "improving insulin sensitivity" in a cell, tissue, or subject means an increase in insulin sensitivity in the cell, tissue, or subject as compared to a reference level (e.g., the insulin sensitivity before employing the method and/or agent).

As used herein, the term "locked nucleic acid" refers to a bicyclic RNA analogue in which the ribose is locked in a C3'-endo conformation by introduction of a 2'-O,4'-C methylene bridge. Desirable LNA monomers and their method of synthesis also are disclosed in U.S. Pat. Nos. 6,043,060, 6,268,490, PCT Publications WO 01/07455, WO 01/00641, WO 98/39352, WO 00/56746, WO 00/56748 and WO 00/66604 as well as in the following papers: Morita et al., Bioorg. Med. Chem. Lett. 12(1):73-76, 2002; Hakansson et al., Bioorg. Med. Chem. Lett. 11(7):935-938, 2001; Koshkin et al., J. Org. Chem. 66(25):8504-8512, 2001; Kvaerno et al., J. Org. Chem. 66(16):5498-5503, 2001; Halkansson et al., J. Org. Chem. 65(17):5161-5166, 2000; Kvaerno et al., J. Org. Chem. 65(17):5167-5176, 2000; Pfundheller et al., Nucleosides Nucleotides 18(9):2017-2030, 1999; and Kumar et al, Bioorg. Med. Chem. Lett. 8(16):2219-2222, 1998.

The term "mixmer" refers to oligonucleotides that comprise both naturally and non-naturally occurring nucleotides. However, there is no contiguous sequence of more than 5 naturally occurring nucleotides.

The term "A*C*A*T/U*G*C*T/U*C*C*A*G*G*T/U*G*A" (SEQ ID NO: 2) refers to an oligonucleotide of said sequence. A*C*A*T/U*G*C*T/U*C*C*A*G*G*T/U*G*A" is the complementary strand of the mi-1983 which associates with miRNA-induced silencing complex.

As used herein, the term "mismatch" refers to one or more mismatched nucleotides in a double stranded region As used herein, the term "diluent" refers to a pharmaceutically acceptable carrier which does not inhibit a physiological activity or property of an active compound to be administered and does not irritate the subject and does not abrogate the biological activity and properties of the administered compound. Diluents include any and all solvents, dispersion media, coatings, surfactants, antioxidants, preservative salts, preservatives, binders, excipients, disintegration agents, lubricants, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated. Diluents that permit or enhance transport of nucleic acids across a cell membrane can also be used.

The term "pre-diabetes" as used herein refers to a condition in which blood glucose levels are higher than normal but are not high enough for a diagnosis of diabetes. Pre-diabetes, is a level of 140 mg/dL to 199 mg/dL 2 hours after the start of an oral glucose tolerance test (OGTT).

As used herein the term "intranasal formulation" refers to a pharmaceutical compositions formulated for intranasal delivery and can be in the form of powders, aqueous solutions, aqueous aerosols, nasal drops, and/or aerosols.

As used herein a "pharmaceutical composition" refers to a preparation of one or more of the active ingredients described herein e.g. the miR-1983 inhibitor with one or more other chemical components such as a physiologically suitable carrier. The purpose of a pharmaceutical composition is to facilitate administration of a compound to an organism.

As used herein, the term "amplifying" refers to any means by which at least a part of a target polynucleotide, target polynucleotide surrogate, or combinations thereof, is reproduced, typically in a template-dependent manner, including without limitation, a broad range of techniques for amplifying nucleic acid sequences, either linearly or exponentially. Exemplary procedures for performing an amplifying step include the polymerase chain reaction (PCR). Descriptions of additional techniques that can be used in the present teachings can be found in, among other places, Sambrook et al. Molecular Cloning, 3$^{rd}$ Edition; Ausbel et al.; PCR Primer: A Laboratory Manual, Diffenbach, Ed., Cold Spring Harbor Press (1995); The Electronic Protocol Book, Chang Bioscience (2002), Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol Diagn. 2002 November; 2(6):542-8., Cook et al., J Microbiol Methods. 2003 May; 53(2):165-74, Schweitzer et al., Curr Opin Biotechnol. 2001 February; 12(1):21-7, U.S. Pat. Nos. 5,830,711, 6,027,889, 5,686,243, Published P.C.T. Application W00056927A3, and Published P.C.T. Application WO9803673A1.

The term "miR-1983 inhibitor" as used herein, is intended to refer to an agent that reduces the intracellular expression or activity of miR-1983. In more detail, the agent acts on miR-1983 directly or on a precursor of miR-1983 indirectly to reduce the expression of microRNA-1983 at the transcription level, promote the degradation of expressed miR-1983, or disrupt the activity of miR-1983, thereby decreasing the expression level or activity of miR-1983. "miR-1983 inhibitor" includes for example anti-miR-1983 oligonucleotides and modified versions thereof comprising for example a label or tag, a stabilizing moiety and/or a transport moiety.

The terms "improving insulin resistance" generally refers to a therapeutic intervention that ameliorates a sign or symptom of insulin resistance or pathological condition after it has begun to develop. "Ameliorating" generally refers to the reduction in the number or severity of signs or symptoms of a disease.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

Compositions and Methods

Studies have implicated miRNAs in metabolic disease, acting individually or in concert with one another (Feng et al., 2016; Hashimoto and Tanaka, 2016; Vienberg et al., 2016). Some have implicated miRNA regulation in mediating insulin sensitivity in hypothalamic tissue. For instance, silencing of miR-200a in the hypothalamus of ob/ob leptin-deficient mice was sufficient in improving both leptin and insulin signaling by increasing both the leptin receptor and InsR substrate 2 (IRS-2) expression levels (Crepin et al., 2014). Also, hypothalamic knockdown of Dicer, one of the essential components of miRNA biogenesis, results in hyperphagic obesity that may be reversed upon intracerebroventricular (ICV) delivery of a mimic of miR-103 (Vinnikov et al., 2014). Studies have implicated miRNAs of the central nervous system (CNS) may have a key role to play in regulating whole body energy homeostasis, and that the hypothalamus may present a miRNA signature characteristic of specific metabolic states that is unique. Such signatures could serve as a diagnostic tool or a therapeutic target in the treatment of human disease. Given the vital importance of insulin signaling to metabolic homeostasis and the key role that hypothalamic neurons play in achieving this balance. The inventors used established in vitro cell to investigate whether neurons exhibit a hallmark miRNA expression profile upon the induction of insulin resistance that concurs with that in the HFD-fed mouse.

It was found that miR-1983 is linked directly to the induction of insulin resistance, and that elevation of miR-1983 in the hypothalamus coincides with increased levels in the serum of mice on a HFD, suggesting that it may be a biomarker for central insulin resistance. Additionally, it was determined that miR-1983 is also present in overweight and obese humans and their serum miR-1983 levels correlate with circulating insulin levels and degree of insulin resistance (Homeostatic model assessment of insulin resistance, HOMA-IR). Finally it was determined that an intranasal transfer of miR-1983 inhibitor restores whole body insulin signaling and glucose homeostasis in mice.

Insulin resistance at the level of the hypothalamus may precede dysregulation of glucose homeostasis. Herein, microRNA miR-1983 was significantly altered during induction of insulin-induced insulin resistance in vitro in feeding-related hypothalamic cell lines with an inverse regulation of insulin receptor (InsR) protein suggesting that InsR is a downstream target of miR-1983. Examination of miR-1983 levels in human serum revealed a positive correlation with measures of insulin resistance, including HOMA-IR. Intranasal exposure to a miR-1983 LNA inhibitor restored peripheral insulin sensitivity and fasting blood glucose levels while preserving InsR protein levels in mice on a HFD. Together, these results implicate miR-1983 as a targetable predictive biomarker for early hypothalamic insulin resistance with the potential to arrest the progression to diabetes.

A first aspect is a miR-1983 inhibitor comprising an anti-miR-1983 oligonucleotide that is complementary to at least part of CTCACCTGGAGCATGTTTTCT (SEQ ID NO: 1), the part comprising at least nucleotides 2 to 8 of CTCACCTGGAGCATGTTTTCT (SEQ ID NO: 1). In an embodiment, the anti-miR-1983 oligonucleotide is complementary to nucleotides 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, or 1 to 8 of SEQ ID NO: 1. In another embodiment, the anti-miR-1983 oligonucleotide is complementary to nucleotides 2 to 21, 2 to 20, 2 to 19, 2 to 18, 2 to 17, 2 to 16, 2 to 15, 2 to 14, 2 to 13, 2 to 12, 2 to 11, 2 to 10, 2 to 9, or 2 to 8 of SEQ ID NO: 1.

In an embodiment, the anti-miR-1983 oligonucleotide is complementary to at least part where the part is or comprises TCACCTGGAGCATGT (SEQ ID NO: 4). In another embodiment the anti-miR-1983 oligonucleotide is complementary to at least part, where the part is or comprises TCACCTGGAGCATG (SEQ ID NO: 5), TCACCTGGAGCAT (SEQ ID NO: 6), TCACCTGGAGCA (SEQ ID NO: 7), TCACCTGGAGC (SEQ ID NO: 8), TCACCTGGAG (SEQ ID NO: 9), TCACCTGGA (SEQ ID NO: 10), TCACCTGG (SEQ ID NO: 11), or TCACCTG (SEQ ID NO: 12). In another embodiment the anti-miR-1983 oligonucleotide is complementary to at least part where the part is or comprises CTCACCTGGAGCATGT (SEQ ID NO: 13), CTCACCTGGAGCATG (SEQ ID NO: 14), CTCACCTGGAGCAT (SEQ ID NO: 15), CTCACCTGGAGCA (SEQ ID NO: 16), CTCACCTGGAGC (SEQ ID NO: 17), CTCACCTGGAG (SEQ ID NO: 18), CTCACCTGGA (SEQ ID NO: 19), CTCACCTGG (SEQ ID NO: 20), or CTCACCTG (SEQ ID NO: 21).

In an embodiment, the anti-miR-1983 oligonucleotide is or comprises nucleotides 9 to 15, 8 to 15, 7 to 15, 6 to 15, 5 to 15, 4 to 15, 3 to 15, 2 to 15, or 1 to 15, nucleotides of SEQ ID NO: 2. The anti-miR 1983 oligonucleotide can also be longer, for example about or up to 21 nucleotides, about or up to 25 nucleotides, about or up to 30 nucleotides, about or up to 35 nucleotides, about or up to 40 nucleotides, about or up to 45 nucleotides, about or up to 50 nucleotides, or, or longer for example up to 132 nucleotides, comprising for example stabilizing sequence for DNA and/or RNA sequences.

In another embodiment, the anti-miR-1983 oligonucleotide comprises RNA monomers. In an embodiment, the anti-miR-1983 oligonucleotide comprises DNA monomers, RNA monomers, LNA monomers or a combination thereof. For example, the anti-miR-1983 oligonucleotide comprises DNA monomers only, RNA monomers only, DNA and LNA monomers, RNA and LNA monomers, or LNA monomers alone.

In another embodiment, the anti-miR-1983 oligonucleotide is chemically modified. For example, the anti-miR-1983 oligonucleotide can comprise one or more chemical modifications that enhance stability in the presence of nucleases. In another embodiment, the anti-miR-1983 oligonucleotide is a chimeric nucleic acid comprising both non-chemically modified and chemically modified nucleotides. In another embodiment, nuclease resistance is also improved by backbone modification of the parent phosphodiester linkages into phosphorothioate linkages in which a sulfur atom replaces one of the non-bridging oxygen atoms in the phosphate group or by using morpholino oligomers, in which a six-membered morpholine ring replaces the sugar moiety. Morpholinos are for example uncharged and inherently resistant to degradation by nucleases.

In another embodiment, the anti-miR-1983 oligonucleotide comprises chemical modification at a 2' position. For example, chemical modification at a 2' position can be synthesized using chemical modification methods including but not limited to "click chemistry" as described in patent US20130116419. The chemically modified nucleic acid can be purchased from different manufacturers. In another embodiment, the chemical modification can be 2'Omethyl (2'O-Me), 2'-O-methoxyethyl (2'O-MOE), 2'fluoro (2'F), locked nucleic acid monomer (LNAM), alkyne functional groups, or other functional groups useful for targeting ligands.

In another embodiment, the anti-miR-1983 oligonucleotide comprises a chemical modification, wherein the modification is selected from 2'Omethyl (2'O-Me), 2'-O-methoxyethyl (2'O-MOE), 2'fluoro (2'F), and locked nucleic acid monomer (LNAM). In another embodiment, the anti-miR-1983 oligonucleotide comprises one or more 2'O-Me chemical modifications. In another embodiment, the anti-miR-1983 oligonucleotide comprises one or more 2'O-MOE chemical modifications. In another embodiment, the anti-miR-1983 oligonucleotide comprises one or more (2'F) chemical modifications. In another embodiment, the anti-miR-1983 oligonucleotide comprises one or more LNAM chemical modifications. In another embodiment, the anti-miR-1983 oligonucleotide comprises a combination of 2'O-Me, 2' O-MOE, and 2'F chemical modifications. In another embodiment, the chemically modified oligonucleotides are synthesized using methods known in the art. In another embodiment, the modified oligonucleotide is purchased from a manufacturer.

In another embodiment, the anti-miR-1983 oligonucleotide comprises chemical modification of a plurality of nucleotide monomers. In an embodiment, the anti-miR-1983 comprises a plurality of chemical modifications of one of 2'O-Me, 2' O-MOE, 2'F or a combination thereof. In another embodiment, the anti-miR-1983 comprises a plurality of only LNAM. In another embodiment, the chemically modified oligonucleotide is purchased from a manufacturer.

In another embodiment, the anti-mRNA 1983 oligonucleotide comprises a plurality of locked nucleic acid monomers (LNAM). In one embodiment, the oligonucleotide comprises one or more LNAs, which are consecutive or separated by one or more non-LNA nucleotides.

In another embodiment, the anti-miR-1983 oligonucleotide is a locked nucleic acid (LNA) or a LNA/DNA mixmer. In one embodiment the mixmer does not contain more than 5 contiguous DNA monomers. In another embodiment, the oligonucleotide comprises LNA and RNA monomers. In another embodiment, no more than 5 contiguous monomers are present. In another embodiment, the oligonucleotide contains locked nucleotides or LNAs containing the 2'-O, 4'-C-methylene ribonucleoside (structure A) wherein the ribose sugar moiety is in a "locked" conformation. In another embodiment, the anti-miR-1983 oligonucleotide contain at least one 2',4'-C-bridged 2' deoxyribonucleoside (CDNA, structure B). See, e.g., U.S. Pat. No. 6,403,566 and Wang et al. (1999) Bioorganic and Medicinal Chemistry Letters, Vol. 9: 1147-1150, both of which are herein incorporated by reference in their entireties.

In another embodiment, the anti-miR-1983 oligonucleotide is a locked nucleic acid (LNA) or a LNA/DNA mixmer wherein the LNA comprises sequence 5'-3', A*C*A*T/U*G*C*T/U*C*C*A*G*G*T/U*G*A (SEQ ID NO: 2), or a part thereof, wherein the part is at least nucleotides 7 nucleotides long and comprises nucleotides at position 9 to 15 of SEQ ID NO: 2. For example when the anti-miR-1983 oligonucleotide is an LNA, the internucleotide linkages (denoted by the asterisk) are phosphorothioate internucleotide linkages.

Locked nucleic acids (LNA™) are a class of high-affinity RNA analogs in which the ribose ring is "locked" in the ideal conformation for Watson-Crick binding. LNA™ oligonucleotides exhibit high thermal stability when hybridized to a complementary DNA or RNA strand. In addition, LNA™ oligonucleotides can be made shorter than traditional DNA or RNA oligonucleotides and still retain a high Tm. LNA™ oligonucleotides can consist of a mixture of LNA™ and DNA or RNA. Incorporation of LNA™ into oligonucleotides has been shown to improve sensitivity and specificity for many hybridization-based technologies including PCR, microarray and in situ hybridization.

In another embodiment, the anti-miR-1983 oligonucleotide comprises only DNA and LNA monomers.

The asterisks denote the internucleotide linkages, optionally phosphodiester or preferably phosphorothioate internucleotide linkages, which form the backbone of LNAs.

In another embodiment, the anti-miR-1983 oligonucleotide is a LNA comprising sequence 5'-3', A*C*A*T*G*C*T*C*C*A*G*G*T*G*A (SEQ ID NO: 2) or a part thereof comprising at least nucleotides 9-15. In another embodiment, the oligonucleotide comprises only RNA and LNA monomers.

In another embodiment, the anti-miR-1983 oligonucleotide is a LNA comprising sequence 5'-3', A*C*A*U*G*C*U*C*C*A*G*G*U*G*A (SEQ ID NO: 2) or a part thereof comprising at least nucleotides 9 to 15. In another embodiment, the oligonucleotide contains one, two, three, or four variant DNA or RNA monomer(s) A*C*A*T/U*G*C*T/U*C*C*A*G*G*T/U*G*A (SEQ ID NO: 2) or in the part thereof comprising at least nucleotides 9-15.

In another embodiment, the anti-miR-1983 oligonucleotide can comprise at least one mismatch and up to 4 mismatches. The mismatch is relative to the miRNA sequence and can for example, be comprised in the middle of the anti-miR oligonucleotide, for example, of 7 monomers. The mismatch can be at anyone of positions 3, 4, 5, or 6.

In another embodiment, the anti-miR-1983 oligonucleotide is double stranded. For example, the anti-miR-1983 oligonucleotide can be synthesized or structured as double stranded molecule and later denatured. In another embodiment, the anti-miR-1983 oligonucleotide is synthesized as single stranded.

In another embodiment, the anti-miR-1983 oligonucleotide is single stranded.

In another embodiment, the anti-miR-1983 oligonucleotide has the same or up to 60%, 70%, 80% or up to 90% sequence identity with the nucleic acid sequence of SEQ ID NO: 2. In certain embodiments, the anti-miR-1983 oligonucleotide has 1, 2, 3, 4, 5, 6, 7, 8, 9 or 10 nucleotide differences from SEQ ID NO: 2. In a further embodiment, the anti-miR-1983 oligonucleotide has the same length, a longer length or a shorter length than miR-1983. In certain embodiments, the anti-miR-1983 oligonucleotide is complementary to the 7 or 8 nucleotides at the 5' end SEQ ID NO: 1. In other embodiments, the anti-miR-1983 oligonucleotide is about or up to 7, 8, 9, 10, 11, 12, 13, 14, 15, 16, 17, 18, 19, 20, 21, 22, 23, 24, 25, 27, 28, 29, 30, 31, 32, 33, 34, 35, 36, 37, 38, 39, 40, 41, 42, 43, 44, 45, 46, 47, 48, 49 or 50 nucleotides in length or any number of nucleotides up to 132 nucleotides or any range derivable therein. In other embodiments, the anti-miR-1983 oligonucleotide is 7-10, 10-20, 20-50, 50-75, 75-100, or 100-132 nucleotides in length or any range derivable therein.

In another embodiment, the miR-1983 inhibitor comprises a marker molecule or tagging molecule such as a fluorescent dye excitable and emitting at UV/VIS or infrared wavelengths like FITC, TRITC, Texas Red, Cy-dyes, alexa dyes (Bioprobes), or the like conjugated to the anti-miR-1983 oligonucleotide.

In an embodiment, the miR-1983 inhibitor comprises a transport moiety attached to one or both ends of the anti-miR-1983 oligonucleotide to facilitate transport across cell membranes and the blood brain barrier. For example, short signal peptides also referred to as protein transduction domains as well as lipophilic groups such as cholesterol domains, lauric acid, and lithoocholic acid derivatives with C32 functionality have been conjugated to oligonucleotides to facilitate their delivery into cells. Other compound that complex with nucleic acids and improve intracellular delivery including lipids such as DOTAP (or other cationic lipid), DDAB, DHDEAB and DOPE, non lipid based polymers such as polyethylenimine, polyamidoamine and dendirmers of these and other polymers. Combinations can also be used. For example in certain embodiments, a combination of lipids is used such as DOTAP and cholesterol or a cholesterol derivative (U.S. Pat. No. 6,770,291, hereby incorporated by reference).

In another embodiment, the miR-1983 inhibitor comprises a stability moiety to increase stability of the inhibitor.

A further aspect is a composition comprising the miR-1983 inhibitor and optionally a diluent. The diluent can be any and all solvents, dispersion media, coatings, surfactants, antioxidants, preservatives (e.g., antibacterial agents, antifungal agents), isotonic agents, salts, preservatives, binders, lubricants, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference) and which can be used with nucleic acids. Except insofar as any conventional carrier is incompatible with the active ingredient, its use in the pharmaceutical compositions is contemplated.

In another embodiment, the composition diluent comprises saline.

In an embodiment, the composition is formulated as an intranasal formulation. In one embodiment, intranasal formulation can be in the form of a powder, aqueous solution, nasal drop, and/or aerosol.

In another embodiment solid formulations for intranasal administration may contain excipients such as lactose, starch or dextran. For example, capsules and cartridges of gelatin for use in an inhaler device or insufflator may be formulated containing a powder mix of the anti-miR-1983 oligonucleotide or composition and a suitable powder excipient such as lactose, starch or dextran. In another embodiment, liquid formulations for intranasal administration may be aqueous or oily solutions for use in the form of aerosols, nasal drops and/or metered spray.

Aerosol formulations can be placed into pressurized acceptable propellant, such as dichlorodifluoromethane, trichlorofluoromethane, dichlorotetrafluoroethane, carbon dioxide, propane, nitrogen or other suitable gasses. The formulation can for example be delivered in the form of an aerosol spray from a pressurized pack, nebulizer or other inhalation device, with the use of a suitable propellant.

In some embodiments, formulations for intranasal administration via inhalation include, but are not limited to a liposomal formulation.

In some embodiments, pharmaceutical compositions for intranasal delivery are administered using an inhalation device. The term "inhalation device" refers to any device that is capable of administering a miR-1983 inhibitor to the nasal passages of the subject. Inhalation devices include devices such as metered dose inhalers (MDIs), dry powder inhalers (DPIs), nebulizers, including jet nebulizers and ultrasonic wave nebulizers, heat vaporizers, soft mist inhalers, thermal aerosol inhalers, and electrohydrodynamic-based solution misting inhaler. Inhalation devices also include high efficiency nebulizers. In some embodiments, a nebulizer is a jet nebulizer, an ultrasonic nebulizer, a pulsating membrane nebulizer, a nebulizer comprising a vibrating mesh or plate with multiple apertures, a nebulizer comprising a vibration generator and an aqueous chamber, or a nebulizer that uses controlled device features to assist inspiratory flow of the aerosolized aqueous solution to the nasal passages of the subject. Nebulizers, metered dose inhalers, and soft mist inhalers deliver pharmaceuticals by forming an aerosol which includes droplet sizes that can easily be inhaled.

In the case of a pressurized aerosol, the dosage unit may be determined by providing a valve to deliver a metered amount. For example, the inhalation device may be a small hard bottle to which a metered dose sprayer is attached.

The miR-1983 inhibitor may also be directly administered to the brain, for example by direct injection (optionally with cannulation) or intracerebroventricular (ICV) administration.

Other modes of delivery can be used, for example wherein the miR-1983 inhibitor comprises a transport moiety. For example, examples of routes of administration include parenteral, e.g. intravenous, subcutaneous, oral and transmucosal.

Another aspect is a method of detecting if a cell is insulin resistant comprising measuring the level of miR-1983 and comparing to a threshold or control, wherein an increased level compared to the control is indicative the cell is insulin resistant. In one embodiment, the control is a mouse cell with normal insulin sensitivity. In another embodiment, the control is a human cell with normal insulin sensitivity.

In another embodiment, the cell is a neuronal cell, optionally a hypothalamic cell. In another embodiment, the cell is a hypothalamic cell. In another embodiment, the cell is a Neuropeptide Y expressing hypothalamic cell.

Another aspect is a method of detecting pre-diabetes or an increased likelihood of developing diabetes in a subject, the method comprising measuring a level of miR-1983 in a biological sample from the subject, wherein an increased level compared to a threshold or control is indicative that the subject has an increased likelihood of developing diabetes. In one embodiment, the control is a mouse cell with normal insulin sensitivity. In another embodiment, the control is a human cell with normal insulin sensitivity.

The level of miRNA in a cell or in a sample can be detected using PCR based methods or with one or more hybridization probes. In an embodiment, measuring the level of miR-1983 comprises using microarray analysis. In another embodiment, a quantitative PCR assay is used to measure the level of miR-1983. In yet a further embodiment, the level of miRNA is detected by isolating miRNA, and hybridized said miRNA with a hybridization probe, for example an antisense molecule described herein.

In another embodiment, measuring the level of miR-1983 comprises (a) polyadenylating the miRNA with ATP and a poly(A) polymerase to form a polyadenylated miRNA having a sequence of contiguous A residues; (b) reverse transcribing the polyadenylated miRNA to form a cDNA in a reaction mixture comprising (i) a first primer of not more than 40 nucleotides in length having complementarity to at least two 3' terminal nucleotides of the miRNA and the sequence of contiguous A residues of the polyadenylated miRNA so as to hybridize therewith and initiate synthesis of a cDNA complementary to the polyadenylated miRNA, (ii) a reverse transcriptase and (iii) all four deoxyribonucleoside triphosphates; (c) amplifying a DNA molecule comprising the cDNA in a reaction mixture comprising (i) the cDNA, (ii) the first primer; (iii) a second primer that is sufficiently complementary to the 3' nucleotides of the cDNA to hybridize therewith and initiate synthesis of an extension product; (iv) a DNA polymerase and (v) all four deoxyribonucleoside triphosphates; and (d) detecting and/or quantifying the amplified DNA molecule, wherein the presence and/or quantity of the amplified DNA corresponds to that of the miRNA. In a further embodiment, the primer used to during the measuring of miRNA levels is designed using the methods described in Balcells et al., 2018. In another embodiment, detecting and/or quantifying the amplified cDNA molecule comprises utilizing real time RT-PCR. In a further embodiment, detecting and/or quantifying the amplified cDNA comprises utilizing gel electrophoresis.

Serum levels of miRNA have been detected. In an embodiment, the biological sample is one of blood, plasma or serum, urine or tissue.

In an embodiment, biological sample is taken from a subject that has fasted for at least 8 hours. In another embodiment, the method further comprises measuring insulin and/or glucose levels. In some embodiments, lipids such as cholesterol and/or LDL are also measured. In some embodiments, the method further comprises measuring a normalized level of miR1983, optionally normalized to the level of an internal control such as snoRNA202.

In an embodiment, the subject is a subject with a BMI of at least 25. In an embodiment, the subject is prediabetic for example not taking insulin or an insulin sensitizer.

As shown in the Examples, detecting miR-1983 or an increased level thereof relative to a pre-determined standard or prior level is predictive for the development of insulin resistance. It is an early marker and precedes development of insulin resistance. It provides an opportunity to identify subjects who may be headed for insulin resistance and thereby provide earlier intervention.

In an embodiment, the biological sample is a serum sample. In another embodiment, the serum sample is retrieved using standard human blood retrieval procedures.

In another embodiment, the level of miR-1983 is measured by a quantitative PCR assay. In another embodiment, other amplifying procedures other than PCR methods are used as described in U.S. Pat. Nos. 5,830,711, 6,027,889, 5,686,243, published P.C.T. Application W00056927A3, and Published P.C.T. Application WO9803673A1 among others.

In another embodiment, the quantitative PCR method comprises generating cDNA from RNA obtained from the cell or biological sample, amplifying the cDNA using sequence specific primers and quantitating the level of miR-1983.

A subject with an increased level of miR-1983 can be monitored for further changes and treated either by diet modification or a treatment suitable for pre-diabetes or diabetes. A subject with increased miR-1983 levels can for example be treated with an anti-miR inhibitor described herein.

Accordingly another aspect is a method of improving insulin sensitivity in a subject, the method comprising administering a miR-1983 inhibitor or a composition comprising said inhibitor to a subject in need thereof. In one embodiment, the subject in need thereof is an animal with insulin resistance or pre-diabetes. In another embodiment, the subject in need thereof is a human with insulin resistance or pre-diabetes. In yet a further embodiment, the subject in need thereof has been diagnosed with diabetes. Any of the miR-1983 inhibitors described herein can be administered, including combinations thereof.

In an embodiment, the subject is administered a miR-1983 inhibitor or a composition comprising said inhibitor when the subject exhibits one or more signs of insulin resistance, for example before any other anti-diabetic drugs would be typically prescribed. In another embodiment the subject is administered a miR-1983 inhibitor in combination with another treatment for insulin resistance or diabetes.

The level of miR1983, can be measured prior to administering the miR-1983 to confirm that levels are elevated. Accordingly in an aspect, a subject with an increased level of miR-1983 is administered a miR-1983 inhibitor.

In one embodiment improving insulin sensitivity refers to achieving a level of insulin sensitivity that is increased by at least 10%, at least 20%, at least 30% or more compared to a baseline level prior to administration of the treatment, for example as measured by intraperitoneal insulin tolerance test (IpITT), optionally where the sensitivity is increased similar relative to a subject without diagnosed insulin resistance.

In another embodiment the miR-1983 inhibitor or composition comprising said inhibitor is administered in a manner that allows contact with and/or targets neurons. In another embodiment, the miR-1983 inhibitor or composition comprising said inhibitor is administered in a manner that allows contact with and/or targets hypothalamic neurons. For example, in some embodiments the miR-1983 inhibitor or composition comprising said inhibitor is administered intranasally.

In an embodiment, the miR-1983 inhibitor administered is an anti-miR-1983 oligonucleotide. In another embodiment, the anti-miR-1983 oligonucleotide administered is comprised in a composition comprising one or more components optionally with a diluent. In another embodiment, the diluent is saline or other diluent described herein.

In another embodiment, the miR-1983 inhibitor or composition comprising said inhibitor is administered intranasally, by patch or intravenously.

The miR-1983 inhibitor can be administered with another therapeutic. In particular the miR-1983 inhibitor can be administered with another therapeutic that is intranasally administered. In one embodiment, the another therapeutic is a leptin.

Also provided are uses of the miR-1983 inhibitors and compositions described herein for treating a subject in need thereof, as described herein.

Also provide is a nasal delivery apparatus comprising a miRNA 1983 inhibitor described herein. In an embodiment the apparatus is a nasal spray pump or a pressurized delivery device.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

EXAMPLES

The following non-limiting examples are illustrative of the present disclosure:

Example 1

Figure 1D:
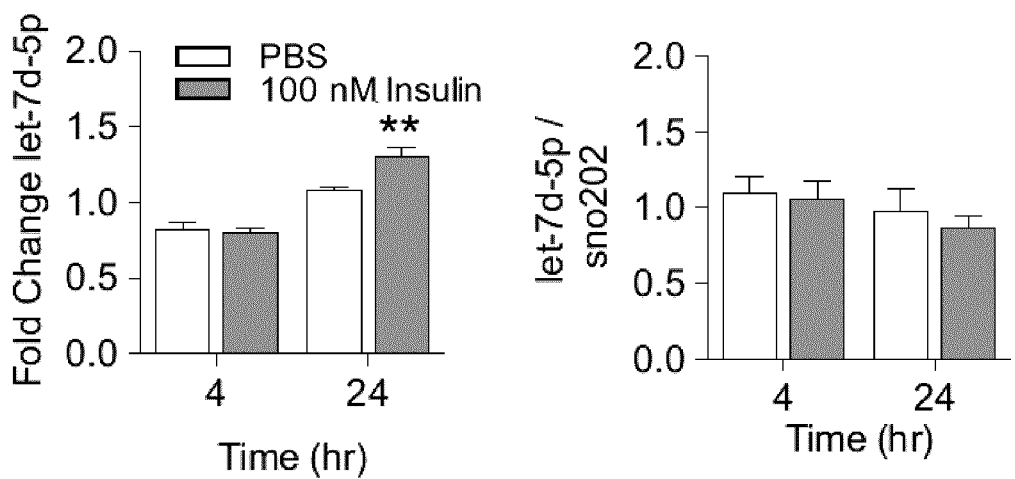

The Induction of Insulin Resistance in a Hypothalamic NPY-Expressing Neuronal Cell Line Induces Changes in miR-1983 and miR-20a-3p Levels The mHypoE-46 cell line, which expresses and secretes NPY and AgRP, has been well characterized for its response to insulin and the mechanisms by which insulin resistance develops at the cellular level have been identified (Mayer and Belsham, 2009, 2010a). Of particular interest, the loss of InsR or InsR substrate 1 (IRS-1) proteins upon the development of insulin resistance did not involve any changes at the mRNA transcript level. This finding suggested that another layer of regulation could exist. It was hypothesized that this could be through miRNAs. miRNAs are small RNA molecules that can sequester mRNAs p-bodies thus preventing protein translation (Bhattacharyya et al., 2006; Liu et al., 2005). To test this hypothesis, and determine on a broader scale if miRNAs were altered by a state of insulin-induced insulin resistance, the mHypoE-46 cells were treated with vehicle or 100 nM of insulin for both 4 and 24 hours and their total RNA was sent for microarray analysis. These time points were chosen in order to distinguish those miRNAs that respond to insulin under normal signaling conditions (after 4 hours) versus those once insulin resistance has been established (after 24 hours). The microarray data revealed that 60 miRNAs were significantly changed across all groups (FIG. 8). Data were then sorted to determine those miRNAs changing only in the insulin-treated groups between 4 and 24 hours (FIG. 9). Twelve miRNAs were found to be significantly different at the 24 hour time point compared to vehicle, and were ranked according to the greatest degree of fold change. The top four miRNAs that were increased at the 24 hour time point were selected for validation by qPCR. In order to confirm the hallmarks of insulin resistance identified by the microarray analysis, the mHypoE-46 cells were treated with vehicle or 100 nM of insulin for 4 and 24 hours and qPCR and Western blotting was performed for the quantification of the InsR mRNA and protein (FIG. 10). qPCR validation of miRNAs revealed that only miR-1983 (FIG. 1A) and miR-20a-3p (FIG. 1B) continued to display an upregulation at 24 hours with 100 nM of insulin treatment, unlike miR-296-5p (FIG. 1C) or Let-7d-5p (FIG. 1D). Based on these findings miR-1983 and miR-20a-3p were then chosen for further experimental analysis. The methods for this example can be found in Example 10.

Example 2 miR-1983 is Differentially Regulated During Insulin Resistance in NPY-Versus POMC-Expressing Cell Lines and is Not Permanently Elevated in NPY Neurons Following the Induction of Insulin Resistance In order to determine if the changes in miR-1983 and miR-20a-3p were unique to the mHypoE-46 (male) cell line, the adult-derived non-clonal mHypoA-NPY/GFP (female) and mHypoA-POMC/GFP-2 (male) cell lines were treated with 100 nM of insulin or vehicle for 16 hours, sufficient to elicit insulin resistance (Wellhauser et al., 2016) (FIGS. 2A and 2B, respectively). Levels of miR-1983 were found to be upregulated in the mHypoA-NPY/GFP cell line suggesting that the elevation of miR-1983 in response to prolonged insulin treatment is conserved among NPY cells regardless of origin (embryonic versus adult) or sex (male versus female).

In light of the discovery that miRNAs may also be differentially expressed among neuronal populations in the ARC (Herzer et al., 2012), it was tested whether the mHypoA-POMC/GFP-2 cell line would also present with the same changes in miR-1983 upon exposure to insulin. Unlike the NPY/AgRP cell models, 16 hours of 100 nM insulin exposure caused a decrease in levels of miR-1983. Thus, despite both NPY/AgRP and POMC models becoming insulin resistant under the given paradigm, the specific miRNAs may differ among these neuronal populations. The observation that the opposite effect of insulin is seen in these two neuronal cell lines is characteristic of the differential signaling observed in these two populations of cells in response to insulin in general (Belgardt et al., 2009), and raises the possibility that the effect of insulin resistance on miR-1983 is unique to NPY expressing neurons. There were no changes in miR-20a-3p in either of mHypoA-NPY/GFP or mHypoA-POMC/GFP-2 cells, indicating that the effects of insulin on this particular miRNA may not be conserved beyond the mHypoE-46 cell line.

Once miR-1983 was defined as a marker of insulin resistance in the mHypoE-46 model, the next step was to determine whether the onset of insulin resistance induced either a transient or permanent alteration in miR-1983 levels. qPCR and Western blot data revealed that after 48 hours of 100 nM insulin treatment levels of the InsR β-subunit remained low despite the return of miR-1983 to normal levels (FIG. 2C). Therefore, in this cell model changes in miR-1983 are in fact transient, occurring within a specific timeframe in response to insulin exposure, indicating that the miR-1983 may likely be a contributor to the progression or development of insulin resistance rather than solely a marker of a final state in which the neurons no longer retain the ability to sense insulin. The methods used in this example can be found in Example 10.

Example 3 miR-1983 Targets the InsR Protein In Vitro

Figure 3A:
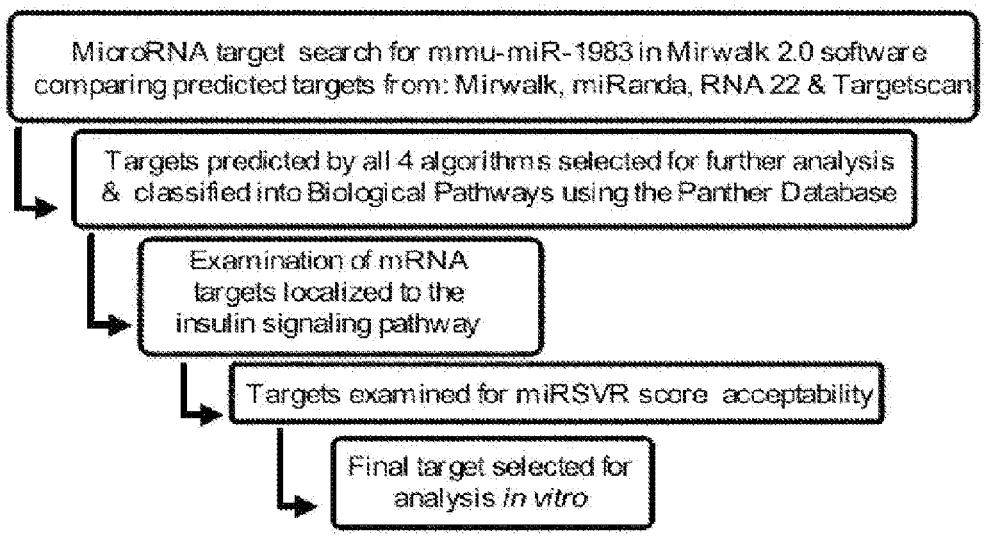
Figure 3B:
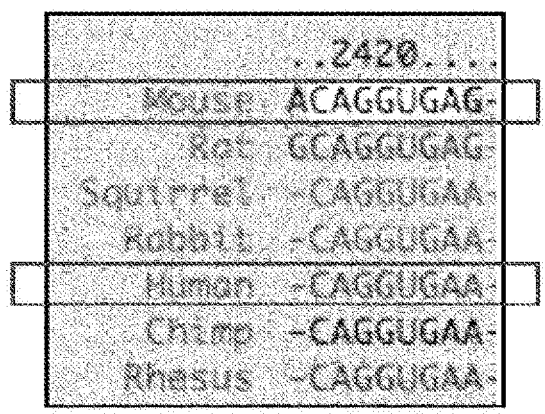

Having established the timeline of miR-1983 regulation by insulin, elucidation of the ultimate mRNA targets and identification of how these targets may contribute to the development of resistance in the mHypoE-46 model was undertaken. In silica bioinformatics analysis revealed that the 3' untranslated region (UTR) of the InsR was a possible target of miR-1983, and that this seed sequence region of the mRNA is also conserved across species, including humans (FIGS. 3A, 3B). Of note, although miR-1983 itself has not yet been recognized in online database resources as being conserved in humans, this miRNA has been discovered to be present and elevated in psoriatic human skin over normal skin (Edinger et al., 2014). More recently, the process by which miR-1983 is uniquely derived from the isoleucine (Ile) pre-transfer RNA (tRNA) to become a fully functional miRNA in human cells has also been described (Hasler et al., 2016).

To assess if miR-1983 could bind to the predicated site in the 3'UTR of the InsR, transient transfections of the pmir-GLO vector containing this region were conducted in the presence of a miR-1983 mimic or negative control. Resulting luciferase assays revealed that the miR-1983 mimic reduced the light units produced by approximately 15% after 48 hrs (FIG. 1F).

Figure 3C:
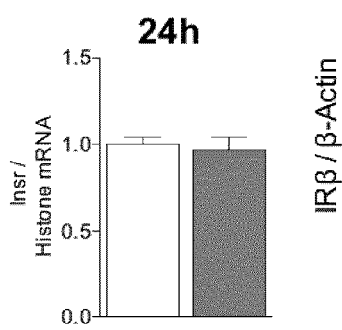
Figure 3D:
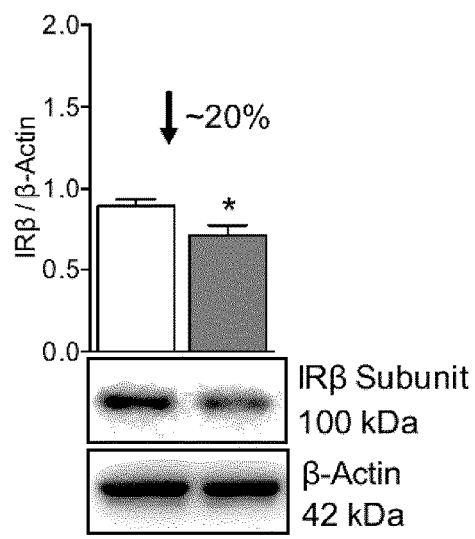
Figure 3E:
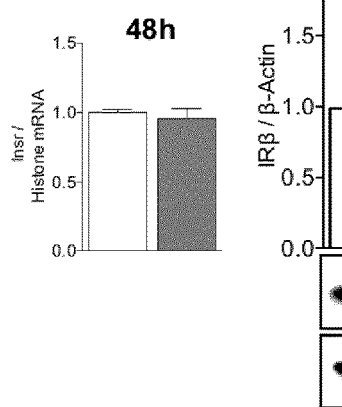
Figure 3F:
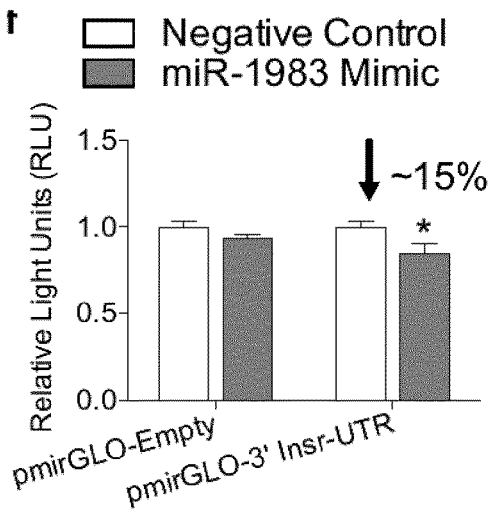

Transfection of the mHypoE-46 neurons with a mimic of miR-1983 resulted in an increase in miR-1983 levels at 24 hours. The increase in miR-1983 observed did not affect the insulin sensitivity or the levels of the InsR mRNA after 24 hours (FIG. 3C). Nevertheless, it was found that upregulation of miR-1983 levels alone were sufficient to decrease the protein levels of the InsR by 20% after 24 hours (FIG. 3D) and by 35% after 48 hrs (FIG. 3E), while InsR mRNA levels after 24 or 48 hrs remained unchanged regardless of time point (FIGS. 3D, and E). This suggests that miR-1983 could contribute to the process by which insulin resistance develops. Collectively, these data combined with prior observations point to miR-1983 as being a marker for early insulin resistance in neurons driven by exposure to high levels of insulin. Ultimately, the next question to be addressed was whether miR-1983 could be regulated in the hypothalamus in an in vivo setting of insulin resistance. Thus the impact of a HFD regimen capable of inducing insulin resistance in mice on miR-1983 levels in the hypothalamus was assessed. The methods used in this example can be found in Example 10.

Example 4

Figure 4A:
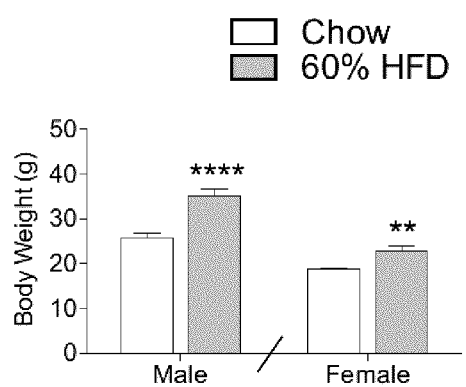
Figure 4B:
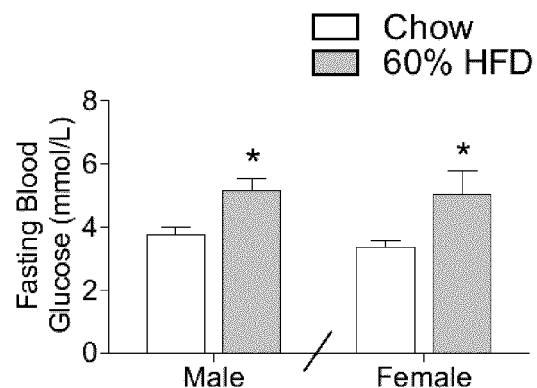
Figure 4C:
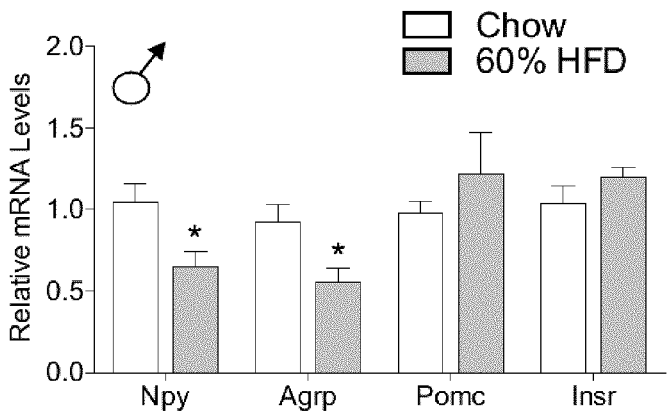
Figure 4D:
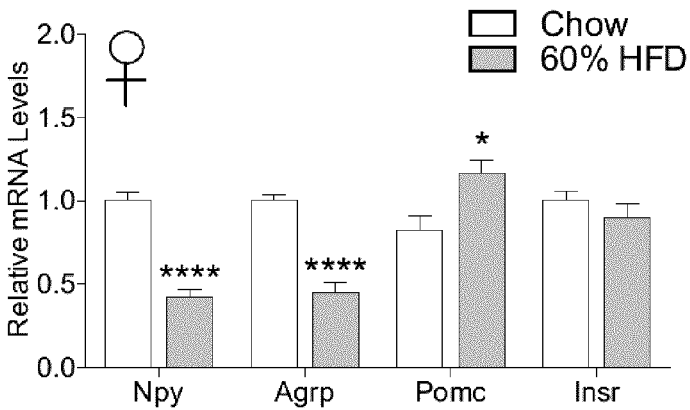
Figure 4E:
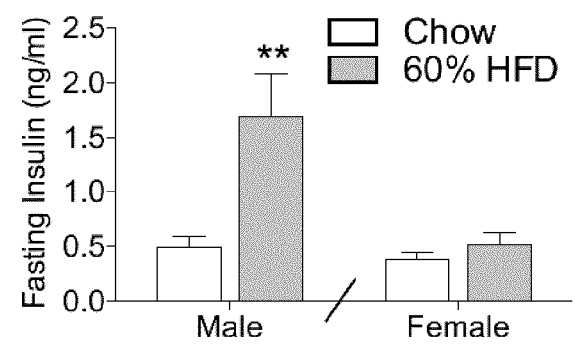
Figure 4F:
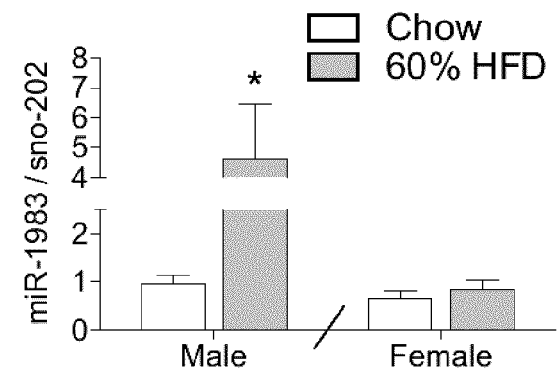

Male C57BL/6 Mice Display an Increase in Hypothalamic miR-1983 After 7-9 Weeks on a 60% HFD Both male and female C57BL/6 mice were placed on a 60% HFD for 7-9 weeks during which both sexes gained significant body weight and displayed increased blood glucose levels (FIGS. 4A & 4B). These peripheral changes were accompanied by decreases in the mRNA levels of both Npy and Agrp in both males and females, and an increase in Pomc in the female mice (FIGS. 4C & 4D). Male C57BL/6 mice displayed an increase in circulating insulin levels at 7 weeks, indicating insulin resistance, and a concomitant increase in miR-1983 in their hypothalamus (FIGS. 4E & 4F). Therefore, in the C57BL/6 mouse strain, it appears that exposure to a 60% HFD only when accompanied with high circulating levels of insulin gives rise to elevated hypothalamic miR-1983 levels. Because the female mice did not yet have an increase in insulin at 7 wks, no change in miR-1983 was detected. There were no changes observed in the mRNA levels of the InsR in either sex (FIGS. 4C & 4D). Given that changes were observed in miR-1983 in vivo in male mice, the next goal was to determine if this was unique to one strain of mouse and to determine whether the timeline associated with this regulation is conserved. The methods used in this example can be found in Example 10.

Example 5

Figure 5A:
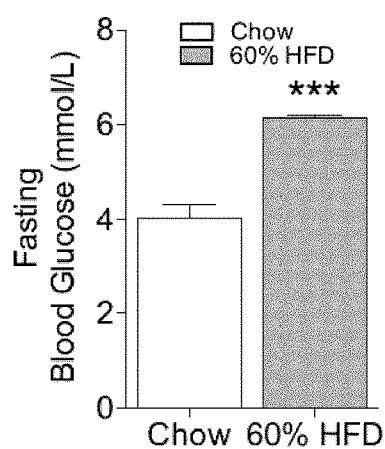
Figure 5B:
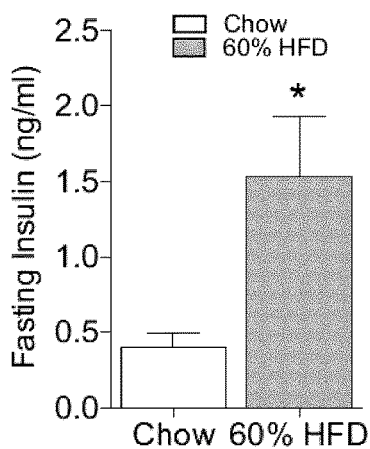
Figure 5C:
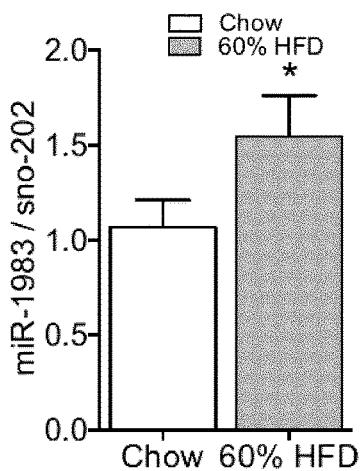
Figure 5D:
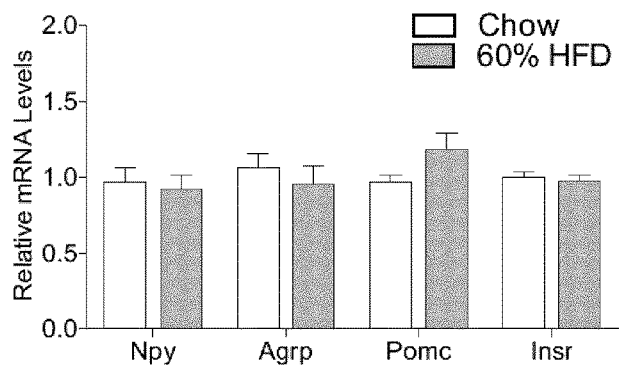
Figure 5E:
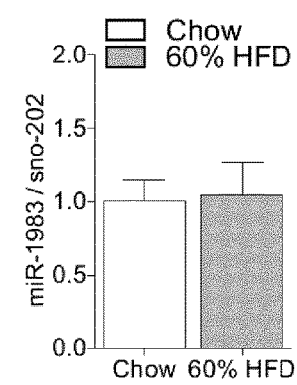
Figure 5F:
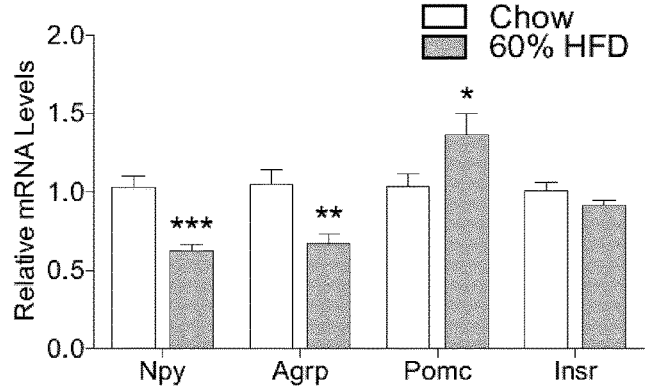

The Elevation Observed in miR-1983 in the Hypothalamus of Male CD-1 Mice Fed a 60% HFD is Dependent on the Length of HFD Exposure Male CD-1 mice are known to develop peripheral insulin resistance between 5-6 weeks on a 60% HFD (Liu et al., 2016), a shorter timeframe compared to the C57BL/6 strain; therefore fasting blood glucose was collected at this time point. It was found that 5 weeks of HFD increased fasting blood glucose (FIG. 5A), circulating insulin (FIG. 5B), and miR-1983 levels in the hypothalamus (FIG. 5C), without causing changes in hypothalamic Npy, AgRP, Pomc or the InsR mRNA (FIG. 5D). When the length of time on the HFD was extended to 10 weeks, there was no longer a difference in miR-1983 levels observed in the hypothalamus between experimental groups (FIG. 5E). However, after 10 weeks, the mRNA levels of Npy and AgRP were decreased and Pomc increased in the mice fed a HFD compared to chow (FIG. 5F). Once again, there were no changes observed in the levels of the Insr mRNA. (FIG. 5F). These data indicated that in male CD-1 mice upregulation of miR-1983 precedes the alterations in neuropeptide levels. Having established the timing of miR-1983 regulation in the male CD-1 mice, the response in female mice within a 5 week time frame of the diet was then studied. The methods used in this example can be found in Example 10.

Example 6

Figure 6A:
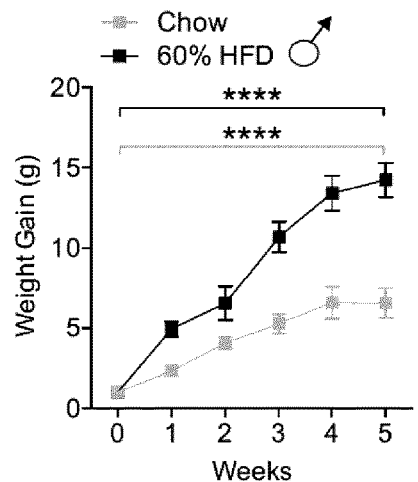
Figure 6B:
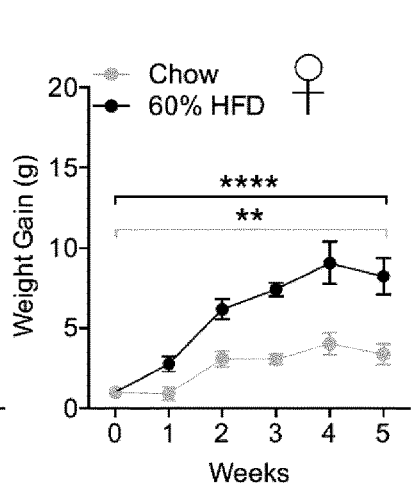
Figure 6C:
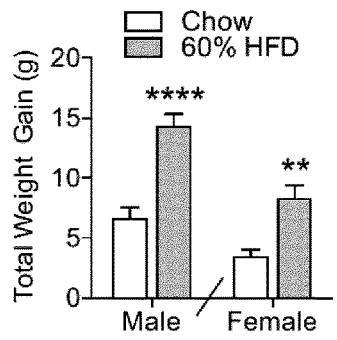
Figure 6D:
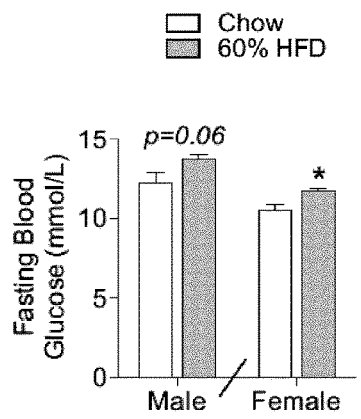
Figure 6E:
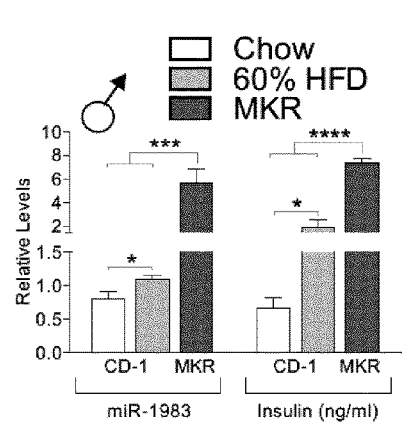
Figure 6F:
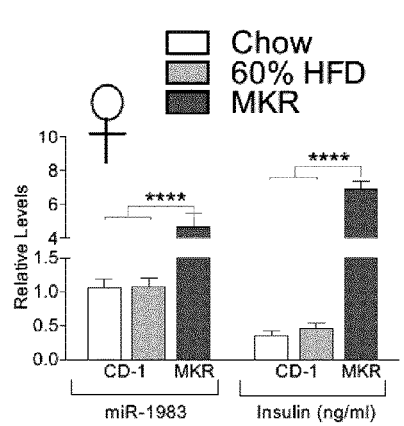
Figure 6G:
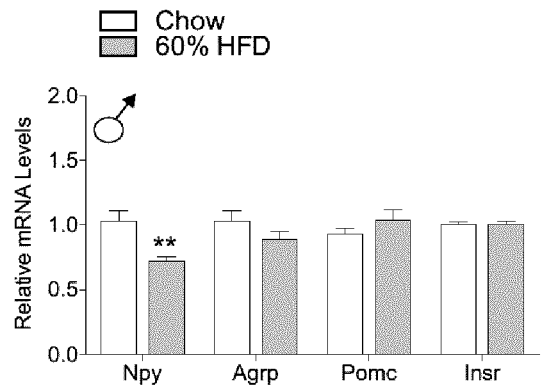
Figure 6H:
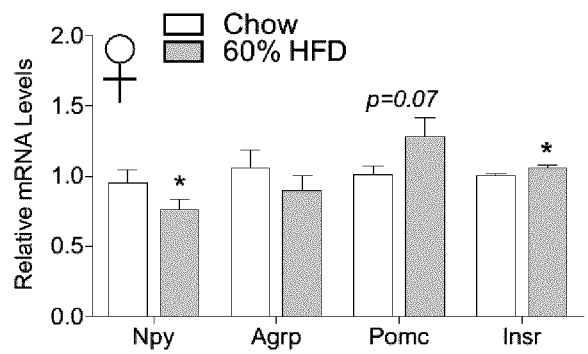
Figure 6I:
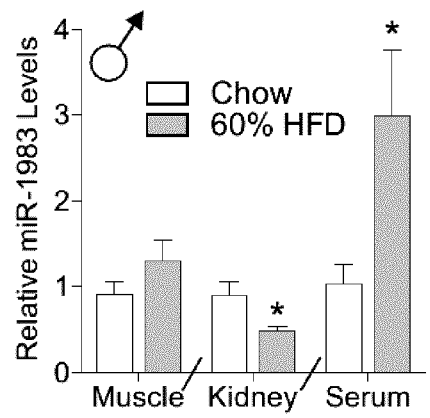

CD-1 Male Mice Display an Increase in miR-1983 in Their Hypothalamus and Serum, but a Decrease in the Kidneys After 5 Weeks on a 60% HFD Over 5 weeks on chow or 60% HFD both male (FIG. 6A) and female (FIG. 6B) CD-1 mice displayed significant weight gain (FIG. 11A), with the total weight gain for both sexes being approximately two-fold greater for the 60% HFD groups (FIGS. 6A and C). Fasting blood glucose was elevated in the female, but not in the male mice (FIG. 6D) and male mice displayed an increase in fasting blood insulin levels and miR-1983 (FIGS. 6E and 6F, respectively). Examination of neuropeptide mRNA levels revealed a decrease in Npy in males and females (FIG. 6G), with an increase of 7% in the InsR mRNA only in the females (FIGS. 6G and 6H). To determine if the increase in miR-1983 in the hypothalamus could be induced by hyperinsulinemia in both male and female mice, independent of a HFD, the hypothalamus from both male and female MKR mice were collected. These mice displayed pronounced elevation of miR-1983 in their hypothalamus in correspondence with comparable levels of circulating plasma insulin when compared to the CD-1 mice without HFD exposure (FIGS. 6E and F).

Having demonstrated changes at the level of the hypothalamus in the male mice, whether there were also changes in miR-1983 in other metabolically relevant tissues, namely the muscle and liver were then assessed. Also, levels in the kidney were also analysed as miR-1983 has been previously found in this tissue in mice, where it is regulated by aldosterone (Edinger et al., 2014). No changes were observed in miR-1983 in the soleus muscle a decrease in the kidney (FIG. 6I), and no detectible levels of this miRNA in the liver.

miRNAs are detectable in the plasma and serum of mice and humans and could be putative biomarkers of metabolic disease. As miR-1983 had previously been detected in the circulation of HFD-fed mice, serum levels were assessed in male CD-1 mice. The levels of miR-1983 were increased nearly three-fold in HFD-fed mouse serum (FIG. 6I), and a significant correlation was detected between insulin levels and miR-1983 in the serum (p=0.03, FIG. 11b).

miRNAs have not only been located in various tissues in the body, they have also been discovered in the plasma and serum of both mice and humans, where they are highly stable due to either their enclosure in exosomes or being bound to proteins, such as Argonaute 2 (AGO2) (Turchinovich et al., 2011; Valadi et al., 2007). As prior miRNA research has also shown that miR-1983 may be detected in the circulation, the levels of miR-1983 in the serum of the male CD-1 mice were assessed (Hsieh et al., 2015). After 5 weeks on a HFD the levels of miR-1983 were found to be increased nearly three-fold in the serum of the male CD-1 mice (FIG. 12B). Therefore, the timing of miR-1983 elevation in the hypothalamus coincides with a detectable increase of levels in the circulation at the 5 week time point.

Given this finding, whether serum levels of miR-1983 could be correlated with other parameters in the blood was investigated. It was discovered that a trend towards a correlation of glucose levels, and a significant correlation between insulin levels with miR-1983 in the serum. This led us to the assessment of if miR-1983 could also be correlated with such parameters in human patients, as outlined in Example 7.

Example 7

Serum Levels of miR-1983 as a Biomarker of Insulin Resistance in Humans

Figure 11A:
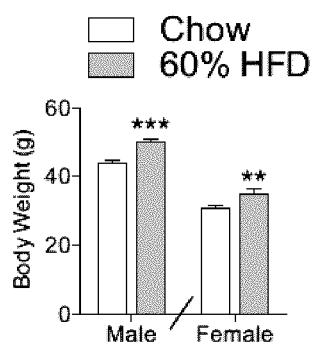
Figure 11B:
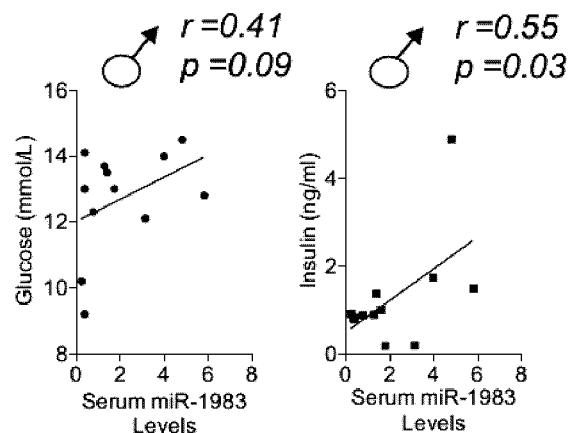
Figure 11C:
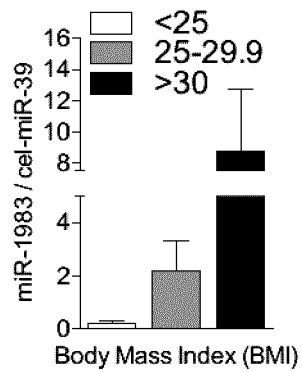
Figure 11D:
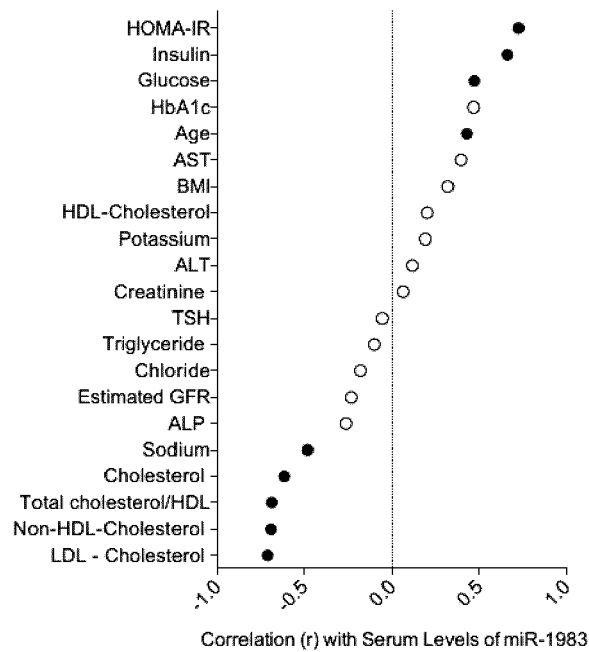
Figure 11E:
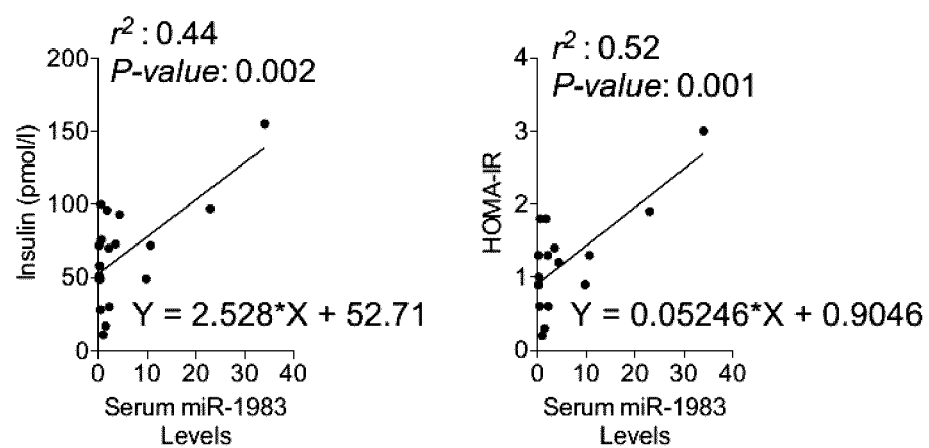

It was shown herein that serum miR-1983 elevations in mice coincide with those in the hypothalamus, suggesting that serum levels may be used as a surrogate for hypothalamic changes.

miR-1983 has been described in humans (Edinger et al., 2014; Hasler et al., 2016). As such it was decided to assay this miRNA in the serum of human subjects.

miR-1983 is correlated with increasing circulating insulin levels and HOMA-IR score.

miR-1983 was detected in all of the human subjects assayed with a body mass index (BMI) greater than 25, those classified as overweight and obese (FIG. 11C). Serum levels of miR-1983 were significantly correlated with various blood parameters (FIG. 11D, Table 1), being most positively associated with increasing insulin and HOMA-IR score as displayed by linear regression analysis (FIG. 11E). These data compliment the finding in mice and support the findings that miR-1983 may serve as a circulating indicator of insulin resistance. The data suggests that miR-1983 can be detected and different stages of developing insulin resistance. Details of the method used are provided in Example 10.

Figure 7A:
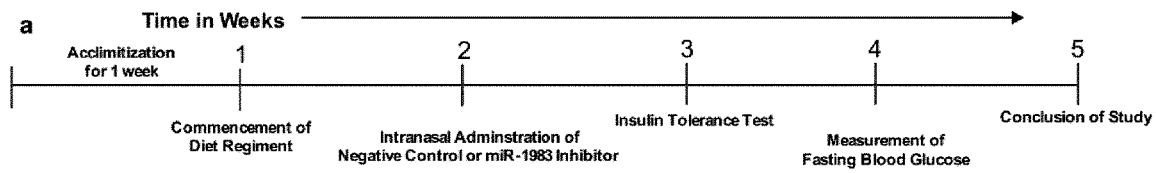
Figure 7B:
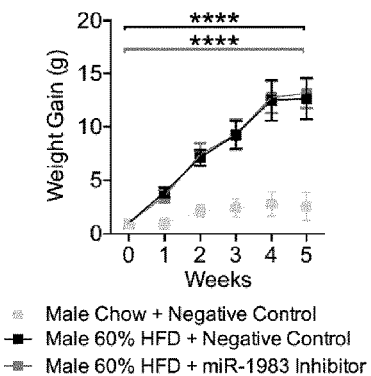
Figure 7C:
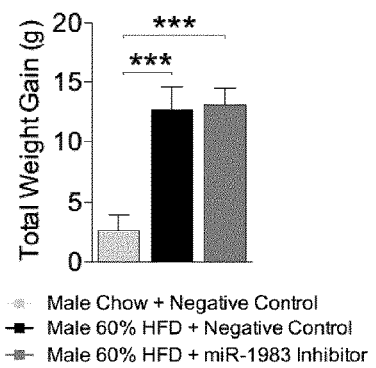
Figure 7D:
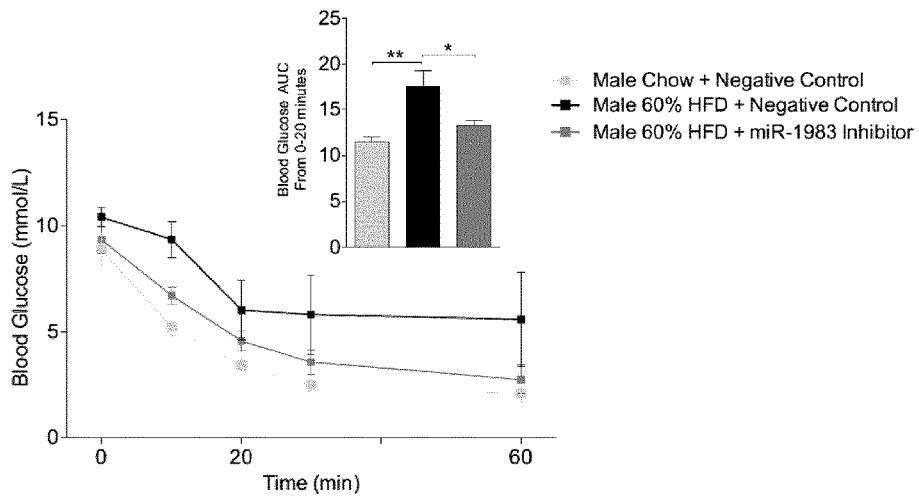
Figure 7E:
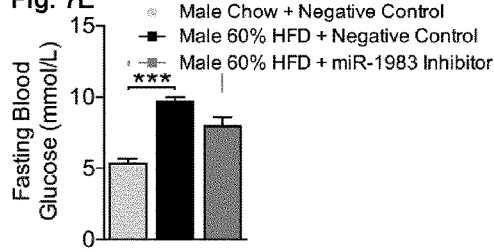
Figure 7F:
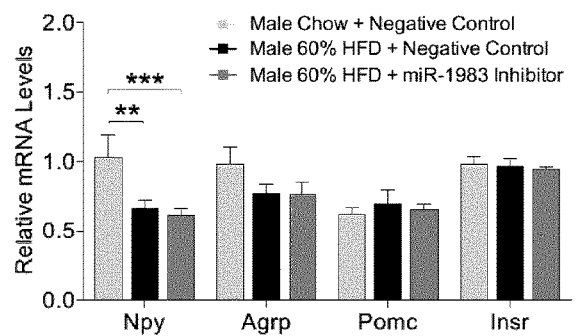

In order to link the in vivo studies to the in vitro finding of InsR regulation by miR-1983, the insulin sensitivity of the mice was examined one week post-intranasal exposure to the inhibitor of miR-1983 or the negative control. A significant improvement in the insulin sensitivity of the inhibitor-treated 60% HFD-fed mice over their counterparts given the negative control at 10 minutes and 20 minutes post intraperitoneal (IP) insulin administration was observed (FIG. 7D). Analysis of the fasting blood glucose for all of the mice two weeks post-intranasal treatment revealed that the HFD-fed group given the inhibitor displayed significantly lower values compared to the HFD-fed negative control group, but as such were still elevated relative to the chow fed animals (FIG. 7E). Upon completion of the 5 week experiment the hypothalamii of the mice were collected revealing that miR-1983 was still decreased in the inhibitor-treated group compared to the negative control and that both of those

TABLE 1

Human serum miR-1983 Correlation Analysis

| Pearson Correlation | r | R squared | P (one-tailed) | P value summary | Significant? (alpha = 0.05) |
|---|---|---|---|---|---|
| HOMA-IR | 0.73 | 0.53 | 0.001 | *** | Yes |
| Insulin (pmol/l) | 0.66 | 0.44 | 0.001 | ** | Yes |
| Glucose (mmol/l) | 0.47 | 0.22 | 0.028 | * | Yes |
| Hemoglobin A1c (HbA1c, mmol/mol) | 0.47 | 0.22 | 0.054 | ns | No |
| Age (yr) | 0.43 | 0.18 | 0.034 | * | Yes |
| Aspartate aminotransferase (AST, U/L) | 0.39 | 0.16 | 0.091 | ns | No |
| BMI (kg/m$^2$) | 0.32 | 0.10 | 0.092 | ns | No |
| High-density lipoprotein (HDL) - Cholesterol (mM) | 0.20 | 0.04 | 0.254 | ns | No |
| Potassium (mM) | 0.19 | 0.04 | 0.277 | ns | No |
| Alanine transaminase (ALT, U/L) | 0.12 | 0.01 | 0.353 | ns | No |
| Creatinine (uM) | −0.06 | 0.00 | 0.432 | ns | No |
| TSH (mIU/L) | −0.06 | 0.00 | 0.432 | ns | No |
| Triglyceride (mM) | −0.10 | 0.01 | 0.372 | ns | No |
| Chloride (mM) | −0.18 | 0.03 | 0.278 | ns | No |
| Estimated Glomerular Filtration Rate (GFR, mL/min/1.73m$^2$) | −0.23 | 0.05 | 0.221 | ns | No |
| Alkaline phosphatase (ALP, U/L) | −0.26 | 0.07 | 0.192 | ns | No |
| Sodium (mM) | −0.48 | 0.23 | 0.047 | * | Yes |
| Cholesterol (mM) | −0.62 | 0.38 | 0.012 | * | Yes |
| Total cholesterol/HDL | −0.69 | 0.48 | 0.005 | ** | Yes |
| Non-HDL-Cholesterol (mM) | −0.69 | 0.48 | 0.006 | ** | Yes |
| Low-density lipoprotein (LDL) - Cholesterol (mM) | −0.71 | 0.51 | 0.003 | ** | Yes |

Example 8

Inhibition of miR-1983 in CD-1 Male Mice Fed a 60% HFD Improves Insulin Sensitivity, Fasting Blood Glucose, and Restores InsR Protein Levels in the Hypothalamus With the knowledge that miR-1983 changes in more than one location in the body in response to a 60% HFD challenge in male CD-1 mice, it was set out to determine the implications of rising miR-1983 levels specifically in the hypothalamus using a directed intranasal exposure of an miR-1983 inhibitor. The methods used in this example can be found in Example 10.

Figure 7G:
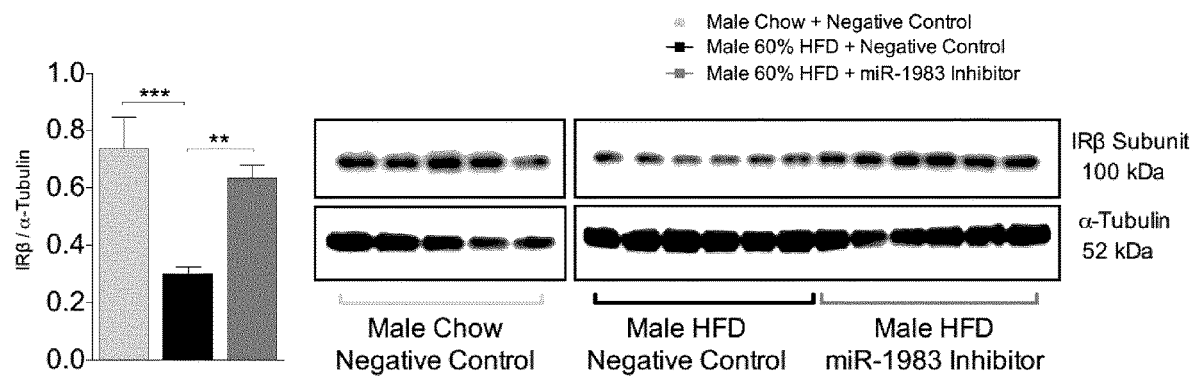

An experimental paradigm was designed to test whether inhibition of miR-1983 specifically in the brain could alter whole body insulin sensitivity upon exposure to a 60% HFD. Both groups of male CD-1 mice fed a 60% HFD and administered the in vivo LNA miRNA miR-1983 inhibitor at a single dose intranasally or the in vivo LNA miRNA negative control (FIG. 7A) gained equal weight over the 5 week experiment compared to the chow group given the in vivo LNA miRNA negative control (FIG. 7B and FIG. 7C).

groups displayed similar mRNA levels of the AgRP, Pomc, and Insr with an similar decrease in Npy mRNA (FIG. 7F) compared to chow controls. As shown in FIG. 7G, miR-1983 inhibitor-treated animals on the HFD had similar levels of InsR protein in the hypothalamus compared to control animals, while those given the negative control had significantly decreased InsR levels corresponding to the increased levels of miR-1983. Overall, these findings suggest that the increased insulin sensitivity observed in the HFD-fed animals receiving the miR-1983 inhibitor is due to retention of InsR protein signaling in the hypothalamus. The methods used in this example can be found in Example 10.

Example: 9

The Inhibition of miR-1983 in Humans Through the Use of Intranasal Administration of miR-1983 Inhibitor Intranasal delivery of in vivo ready miR-1983 LNA inhibitor produced by Exiqon (SEQ ID NO: 2), in general researchers have administered these inhibitors to the brain via stereotaxic cannulation and injection or intracerebroventricular (ICV) have the potential to be used in humans to selectively target the hypothalamus by bypassing the blood brain or CSF-brain barrier (Born et al., 2002; Dhuria et al., 2010). Evidence suggests that intranasal administration of a number of peptides reaches the hypothalamus at high penetration, thus allowing the arcuate nucleus to be targeted with the anti-miRNA in the present study (Meredith et al., 2015). While not commonly used compared to ICV administration, intranasal administration methodology has been successful in determining the role of miR-206 to regulate brain derived neurotrophic factor (BDNF) in the mouse brain (Lee et al., 2012). The results demonstrated that a single dose of the miR-1983 inhibitor given after two weeks of exposure to a HFD was sufficient to improve insulin sensitivity as measured by intraperitoneal insulin tolerance test (IpITT) test one week later and to lower fasting blood glucose after two weeks as compared to the group receiving the control LNA (FIG. 7D). A significant improvement in insulin sensitivity was observed with only a single exposure to the miR-1983 inhibitor. LNA miR inhibitors have increased stability compared to unmodified oligonucleotides, which may explain the long-lasting effects of these drugs in vivo. The administration of the anti-miR-1983 oligonucleotide also prevented the decrease in InsR protein levels in the hypothalamus of the male HFD-fed CD-1 mice (FIG. 7G), further supporting the in vitro data implicating the InsR as a downstream target of this miRNA.

Example 10

Methods

Cell Models and Culture Conditions

The murine mHypoE-46 (male), mHypoA-NPY/GFP (female), mHypoA-POMC/GFP-2 (male) cell lines were cultured in 5.5 mM glucose Dulbecco's modified eagles medium (DMEM; Sigma-Aldrich, St. Louis Mo., USA) supplemented with 5% Fetal Bovine Serum (FBS; (Gibco, Thermofisher Scientific, Waltham, Mass.), and 1% Penicillin-Streptomycin (Gibco) at 37° C. with 5% $CO_2$, as described previously (Belsham et al., 2004; Dhillon et al., 2011; Mayer and Belsham, 2009, 2010a; Nazarians-Armavil et al., 2014; Wellhauser et al., 2016).

Animal Models

Male and female mice of the C57Bl/6, CD-1 and MKR strains were purchased from Charles River Laboratories (Montreal, QC, Canada) at 7 weeks of age and allowed to acclimatize for one week prior to the commencement of experiments. Mice were kept on 12:12 light-dark schedule (7 am-7 pm). All animal experiments were conducted with the approval of the animal care committee at the University of Toronto. CD-1 and C57BL/6 mice were fed either 60% kcal from fat diet (60% HFD) or control (7% sucrose matched) diets (D12492 and D12450J respectively, Research Diets, Inc, New Brunswick, N.J., USA). MKR mice were fed Teklad Diet 8664 (Envigo, Madison, Wis., USA). Where indicated, mice were weighed weekly to track their weight gain over the course of the 5 weeks diet exposure. All animals were euthanized with isoflurane, after a 4-16 hour fast (as stated in figure legends), tissues and blood were then collected and stored at −80° C. until processed for analysis. Blood collected to assay insulin levels were collected using heparin coated syringes after which samples were spun at 6,000×g at 4° C. for 10 minutes wherein plasma was isolated and stored at −80 C. Serum samples were retrieved under anesthesia via cardiac puncture and allowed to clot on ice for 1 hour, then centrifuged at 3,000×g for 10 minutes (Hsieh et al., 2015) after which samples were also stored at −80 C. Hypothalamic tissues from initial cohorts of CD-1 (male) and C57 (male and female) mice were obtained, and further details of metabolic parameters from these mice are published (Liu et al., 2016; Prentice et al., 2014).

Human Patient Study Participants

The human patient study was approved by the University Health Network Research Ethics Board and was conducted in compliance with the Declaration of Helsinki. Subjects with varying body mass indices (BMI) and insulin sensitivities were recruited. A total of 24 subjects were included in the study. In total there were 11 males (m) and 13 females (f) sorted by BMI as, less than 25 (m=2, f=4), between 25-29 (m=6, f=3), and greater than 30 (m=3, f=6). Serum was collected in the overnight-fasted state, in non-coated tubes, allowed to clot, and spun at 3,000×g for 15 min at 4° C. Serum was then immediately frozen at −20° C., then moved to −80° C. for long term storage. Measurements of circulating glucose were measured by glucose meter. Circulating insulin was measured via Elisa on the Abbott Architect i2000 system at the Toronto General Hospital (TGH) core laboratory or by the HI-14K|Human Insulin-Specific radio-immunoassay from EMD Millipore according to manufacturer's directions (Etobicoke, ON, Canada). The Core lab at TGH assayed all other circulating blood parameters listed. No subjects included in the study were taking insulin or insulin sensitizers. Homeostatic model assessments of insulin resistance (HOMA-IR) scores were determined using the HOMA2 model (Levy et al., 1998).

Intranasal Administration of miR-1983 Inhibitor or Control In Vivo

After an acclimatization period, mice were placed on control diet or 60% HFD for two weeks. On the last day of the two week period, mice were administered custom in vivo locked nucleic acid (LNA) miR-1983 inhibitor (5'-3', A*C*A*T*G*C*T*C*C*A*G*G*T*G*A) (SEQ ID NO: 2), or negative control (5'-3', A*C*G*T*C*T*A*T*A*C*G*C*C*C*A) (SEQ ID NO: 3), synthesized by Exiqon (Woburn, Mass., USA) dissolved in sterile 0.9% saline to a concentration of 1 nmol/ul. Mice were anesthetized via isoflurane as described above, placed in a sternal position and administered a total of 10 nmol of either miR-1983 inhibitor or negative control in a total of 10 ul volume intranasally. In order to minimize impact on respiration of the mice, while maximizing retention of the treatment in the nasal cavity, 2.5 ul of the inhibitor or negative control was administered per dose in pairs of mice and with two minutes between each droplet. Mice were placed in a sternal position while under anesthesia. Mice were then recovered from anesthesia and returned to a clean home cage and allowed to continue on their diet regiment. After one and two weeks post treatment the mice underwent intraperitoneal insulin tolerance tests (IpITTs). After a total of 5 weeks on the diet regiment the mice were euthanized (as detailed above) and tissues and serum were collected and stored at −80° C.

Intraperitoneal Insulin Tolerance Test (IpITT)

Mice were fasted for 4 hours prior to the insulin tolerance test and blood glucose measurements. EMLA cream (lidocaine 2.5% and prilocaine 2.5%, AztraZeneca) was applied to the tip of their tail and allowed to take effect before a ≤1 mm was snipped from their tail to allow for blood droplet collection. Basal blood glucose samples were obtained by milking the tail, and applying a droplet of blood to glucose strips inserted into a glucometer (Bayer Contour USB). The mice were then injected with 1 international unit (IU) of insulin per kg body weight (Humulin R, Eli-lily). Further, blood glucose measurements were taken at subsequent time points (10, 20, 30, 60, and 120 minutes). Insulin was prepared by diluting stock Humulin in filter sterilized (0.22 µm) 0.1% free fatty acid free bovine serum albumin (BSA) in 0.9% saline. The commencement of fasting for blood glucose measurements and the insulin tolerance test on the mice were conducted at approximately the same time of day for all experiments.

Microarray Experiment: Analysis & Validation

The mHypoE-46 cell line was treated with sterile 1× phosphate buffered saline (PBS, vehicle control) or 100 nM insulin (Novorapid Insulin, Novonordisk, Mississauga, ON, Canada) for 4 and 24 hours after which miRNAs were harvested and isolated with the Mirvana miRNA isolation kit (Ambion, Thermofisher Scientific, Waltham, Mass.) according to manufacturer instructions. The mHypoA-NPY/GFP and mHypoA-POMC/GFP-2 cell lines were also treated with 100 nM insulin for 16 hrs to examine miR-1983 expression, a time point sufficient to cause insulin resistance in these lines based on prior work. Total RNA was assessed for quantity and quality on a Nanodrop 2000c spectrophotometer (Thermofisher Scientific) prior to submission to the Princess Margaret Genomics Centre for miRNA analysis on the Nanostring nCounter analysis system for mouse miRNA and mouse-associated viral miRNAs, based on miRBase v15 containing 620 probes. Initial assessment of quality and normalization of data were conducted at the MicroArray Centre using nSolver Analysis software NanoString v1.0 by Nanostring Technologies (Seattle, Wash.). Code counts were normalized to the positive controls using the geometric mean method to compute the normalization factor. Next, CodeSet content normalization was performed using the top 100 genes and the geometric mean method to calculate the normalization factor. The normalized code counts were converted to log 2 values for statistical analysis. Upon receipt of microarray results, experiments in the mHypoE-46 cells were repeated and RNA isolation conducted using Purelink Mini RNA isolation columns (Ambion, Thermofisher Scientific, Waltham, Mass.). DNase treatment was performed during RNA isolation using on-column Purelink DNase as per directions from the manufacturer (Thermofisher Scientific). RNA was quantified and assessed for purity on the Nanodrop 2000c spectrophotometer (Thermofisher Scientific).

miRNA Target Identification miRNA targets were identified using Mirwalk 2.0 software (Dweep and Gretz, 2015; Dweep et al., 2011). Potential targets appearing in all four algorithms (mirWalk, miRanda (Betel et al., 2010; Betel et al., 2008), RNA22(Miranda et al., 2006) and Targetscan (Lewis et al., 2005)) were selected for classification into pathways of interest using pantherdb.org (Mi et al., 2013; Mi et al., 2016). The mRNA targets found to be involved in the insulin signaling pathway were selected for further investigation. miRNA targets were validated as having good miRSVR scores according to the accepted literature (Betel et al., 2010) and target sites similar between human and mouse mRNA sequences were identified using Targetscan mouse (Agarwal et al., 2015; Lewis et al., 2005).

Reverse Transcription (RT), Quantitative PCR (qPCR) and Primer Design for mRNA Analysis For mRNA analyses, 500 ng to 1 µg of total RNA was utilized for first-strand cDNA synthesis via the ABI high capacity cDNA archive kit following manufacturer's instructions. qPCR was conducted using the Platinum® SYBR® Green qPCR SuperMix-UDG w/ROX (Thermofisher Scientific), and primers designed using Primer Quest online tool (Integrated DNA Technologies (IDT), Coralville, Iowa). See Table 2 for primer sequences. For all cell lines, samples of 12.5 or 25 ng of cDNA were loaded in triplicate in 10 ul reactions for qPCR and a dose curve of 25, 12,5, 6.25, 3.125 ng was used to calculate absolute RNA values. For all animal tissues samples of 25 ng of cDNA were loaded in triplicate reactions and the delta delta CT method (Livak and Schmittgen, 2001) was used to calculate relative fold change between animal groups. Total mRNA levels of all genes were normalized to Histone 3a for analyses. Samples were loaded onto a 384-well plate and sealed with an optical adhesive cover (both from Applied Biosystems (ABI, Foster City, Calif.). Plates were run on an ABI 7900HT Thermal Cycler under the following conditions; 50° C. for 2 minutes, 95° C. for 2 minutes, then 40 cycles of 95° C. 15 seconds and 60° C. for 1 minute followed by a melt curve at 95° C. for 15 seconds, 60° C. for 15 seconds and 95° C. for 15 seconds. Output from the ABI 7900HT thermal cycler was analyzed using ABI Prism 7000 SDS 2.4 software (ABI).

TABLE 2

Quantitative PCR, Cloning, and Sequencing Primer Sequences

| qPCR Primers | Forward 5' → 3' | Reverse 5' → 3' |
| --- | --- | --- |
| AgRP | CGGAGGTGCTAGATCCACAGA (SEQ ID NO: 22) | AGGACTCGTGCAGCCTTACAC (SEQ ID NO: 23 |
| Histone 3a | CGCTTCCAGAGTGCAGCTATT (SEQ ID NO: 24) | ATCTTCAAAAAGGCCAACCAGAT (SEQ ID NO: 25) |
| Insulin Receptor | TCCCATCAAATATTGCCAAAA TT (SEQ ID NO: 26) | CAGAAATAGATAAATACTTCCAAT CAC (SEQ ID NO: 27) |

TABLE 2-continued

Quantitative PCR, Cloning, and Sequencing Primer Sequences

| | | |
|---|---|---|
| NPY | CAGAAAACGCCCCCAGAA (SEQ ID NO: 28) | AAAAGTCGGGAGAACAAGTTTCAT T (SEQ ID NO: 29) |
| POMC | CCCGCCCAAGGACAAGCGTT (SEQ ID NO: 30) | CTGGCCCTTCTTGTGCGCGT (SEQ ID NO: 31) |

Cloning Primers

| | | |
|---|---|---|
| Insr 3'UTR + SacI site(Bold Letters) | Forward 5' → 3' TTGTCTGCATGAGCTCTCAGAAGTCTTGCTCAGGTG (SEQ ID NO: 32) | |
| Insr 3'UTR + SalI site (Bold Letters) | Reverse 5' → 3' CGGTCTGACCCGTCGACACCATCATTCATTTACCAAG (SEQ ID NO: 33) | |

Sequencing Primers

| | Forward 5' → 3' | Reverse 5' → 3' |
|---|---|---|
| pmirGLO | GATCGCCGTGTAATTCTAGT (SEQ ID NO: 34) | CCAACTCAGCTTCCTTTCGG (SEQ ID NO: 35) |
| miR-1983 binding site region | ATGTTGCCAGGGAACTCAAT (SEQ ID NO: 36) | |

RT-PCR for miRNA Analysis

For miRNA analysis, 100-250 ng of total RNA was used to generate cDNA using the Taqman® miRNA Reverse Transcription Kit (Thermofisher Scientific) and Taqman® miRNA Assay specific primers for RT and qPCR reactions for miR-1983 (ID:121204_mat), miR-20a-3p (ID:002491), miR-296-5p (ID:000527), and Let-7d-5p (ID:002283). qPCR was conducted by loading 25 ng of cDNA in triplicate 10 ul reactions with Taqman® Fast Advanced Master mix (Thermofisher Scientific). Plates were run on an ABI 7900HT thermal cycler under the following conditions: 50° C. for 2 minutes, 95° C. 20 seconds, 40 cycles of 95° C. for 1 second and 60° C. for 20 seconds. The delta-delta CT method was used to calculate relative fold change between groups. miRNA levels were normalized to snoRNA202 (ID:001232) levels as an internal control (Livak and Schmittgen, 2001).

miRNA Isolation from Mouse Serum RT-qPCR

Serum samples were isolated using the Ambion® PARIS Kit (Thermofisher Scientific). Briefly, samples were thawed on ice and 200 ul of each sample was combined with 2× denaturing solution and incubated on ice for 5 minutes. After which, 25 fmol of cel-miR-39-3p RNA (Sequence 5'→3'; UCACCGGGUGUAAAUCAGCUUG (SEQ ID NO: 37), synthesized by IDT was added to each sample to serve as an internal control to normalize miRNA levels (Li and Kowdley, 2012). cDNA was synthesized using the TaqMan Advanced miRNA cDNA synthesis kit, and qPCR was conducted in 10 ul reactions in triplicate using TaqMan Advanced miRNA assays for miR-1983 (Table 3) and cel-mir-39 (ID: 478293_mir) and Taqman Fast Advanced master mix according to specifications of the manufacturer's protocol. Human serum samples were also assayed for the presence of known circulating human microRNAs (Villard et al., 2015) miR-142-3p (TaqMan ID: 477910) and miR-222-3p (Taqman ID: 477982) data not shown. Samples were loaded into plates (as indicated above) and were run on an ABI 7900HT thermal cycler under the following conditions; 95° C. 20 seconds, 40 cycles at 95° C. for 1 second, and 60° C. for 20 seconds. Comparison of experimental groups was conducted via the delta-delta CT method (Livak and Schmittgen, 2001).

TABLE 3

Nucleotide sequences of mouse miR-1983 and human miR-1983

| Species | Nucleotide sequence 5' to 3' |
|---|---|
| Mouse miR-1983 | CTCACCTGGAGCATGTTTTCT (SEQ ID NO: 1) |
| Human miR-1983 | CTCACCTGGAGCATGTTTTCT (SEQ ID NO: 1) |

Human miR-1983 is found on chromosome 6 and mouse miR-1983 is found on chromosome 13. Rhesus Macaques have the same miRNA-1983 sequence (found on chromosome 4).

miRNA-1983 Mimic Transfections in mHypoE-46 Cells mHypoE-46 cells were cultured in 100 mm tissue culture dishes to 70-75% confluency, 25 nM of miRNA-1983 mimic or negative control (Thermofisher Scientific) was transfected into mHypoE-46 cells using 5 ug/ml of Dharmafect 3 (Dharmacon, GE, location) according to manufacturer's specifications for 24 hours or 48 hours. Cells were then washed with 1×PBS and placed into serum free 5.5 mM DMEM (Sigma-Aldrich, St. Louis Mo., USA) for 1 hour prior to being re-challenged with 10 nM of insulin for 15 minutes. Cells were washed with ice-cold 1×PBS followed by the isolation of total protein and RNA (containing miRNAs) using the Ambion® PARIS Kit according to specifications of the manufacturer.

Cloning of the Insr 3'UTR into pmirGLO and Co-Transfections of Construct and miRNA-1983 Mimic in mHypoE-46 Cells The 3'UTR of the Insr gene was amplified from mouse genomic DNA (Genomic DNA Purification Kit, Thermofisher Scientific) with primers designed to add restriction enzyme sites complimentary to the multiple cloning site of the pmirGLO vector (Promega corporation, Madison Wis., USA). After restriction digest of both the vector and 3'UTR, the two were ligated and transformed into HB101 competent cells. Bacterial colonies that were ampicillin resistant were selected and grown to isolate DNA to confirm the presence of the insert in the correct orientation. Restriction enzymes and buffers were purchased from cell signaling technology Inc. (Danvers, Mass., USA). Vector DNA containing the 3'UTR Insr insert was sent for sequencing (for primers see Table 2) at the Centre for Applied Genomics (TCAG, Toronto, ON, Canada). For transfections, the mHypoE-46 cells were cultured to 70-75% confluency in 6 well plates (Sarstedt, Montreal, QC, Canada). Then 25 nM of miRNA-1983 mimic or negative control (as used above) and 5 ug of pmiRGLO-Empty or 3'UTR Insr was transfected using 6 ul of Turbofect per well (Dharmacon, GE, location) according to manufacturer's specifications for 48 hrs. Cells were washed once with ice-cold 1×PBS after which cells were lysed in 450 ul passive lysis buffer per well (Biotium Inc., Fremont, Calif., USA) according to manufacturer's instructions.

Protein Isolation, SDS-PAGE and Western Blotting

Protein was isolated as previously described (Nazarians-Armavil et al., 2014) or using the Ambion® PARIS Kit according to manufacturer's specifications and quantified using bicincchoninic acid (BCA) protein assay kit (Pierce, Thermofisher Scientific). For Western blotting, 15-25 ug of protein (sample buffer Biorad, TCEP bond breaker solution) (Thermofisher Scientific, Waltham, Mass., USA for boiling) for each sample was resolved on 10% Bis-Acrylamide-Tris gels and transferred onto 0.2 µm polyvinylidene fluoride (PVDF) Immun-Blot membranes (Bio-Rad, Hercules, Calif., USA) using the iBlot 2 dry blotting system (Thermofisher Scientific). Antibodies (rabbit anti-mouse) for InsRβ-subunit, α-tubulin, phosphorylated AKT and total AKT, along with rabbit secondary antibody IgG, and Signalfire elite ECL reagent were purchased from cell signaling technology Inc. (Danvers, Mass., USA). The β-Actin antibody used as a loading control was purchased from Sigma-Aldrich. All primary antibodies (1:1000) were incubated overnight at 4° C. in 5% non-fat milk in tris-buffered saline with 0.1% Tween-20 (TBS-T). An anti-rabbit secondary antibody (1:7500) was then used, and incubated in 5% non-fat milk in 1× TBS-T for 2 hours at room temperature. Blots were then washed with 0.1% TBS-T for 30 minutes and imaged on Kodak Imaging 3000 station Eastman Kodak Company, Rochester, N.Y.). For total AKT detection, blots were stripped using restore plus stripping buffer (Thermofisher Scientific) as directed, and re-probed. Western blotting for mouse hypothalamic tissue was conducted such that all groups were processed, run on gels, incubated with antibodies and imaged together at the same time. Densitometry was conducted using Image J Software (Image J software, NIH, Bethesda, Md., USA, http://imagej.nih.gov.ij/).

Palmitate Treatment of the mHypoE-46 Cell Line

The mHypoE-46 cell line was treated with either sterile water or 50 µM of sodium palmitate (Sigma-Aldrich) for 24 hours. Sodium palmitate solution was prepared by combining the powder and sterile water and heating the mixture to 65° C. until completely dissolved. The solution was then added directly to warm (37° C.) cell culture media and the cells treated immediately. Assessment of miR-1983 levels was completed as described above.

Statistical Analysis

All data were analyzed using GraphPad Prism Version 6.0c. A students t-test, one or two-way ANOVA followed by Bonferroni or Fisher's LSD post-hoc analyses were conducted, as described. Data were considered to be statistically significant where the p-value was found to be p<0.05. All data are presented as ±SEM.

Example 11

An important consideration for potential applications is whether or not they apply to both sexes. C57Bl/6 female mice displayed a similar pattern in neuropeptide levels following exposure to a HFD, that were comparable in direction and magnitude to that observed by female C56Bl/6 mice fed a 35% HFD for 12 weeks (Lee et al., 2010). CD-1 female mice displayed the same changes in NPY compared to their male counterparts in the study after 5 weeks matching that seen in the female C56Bl/6 mice after 7-9 weeks of exposure to the HFD. Overall, the respective compensatory alterations in Npy and Pomc mRNA levels observed in these studies are similar to those previously reported (Bergen et al., 1999). While clear upregulation of miR-1983 in the adult female mHypoA-NPY/GFP cell model following insulin exposure was observed, the same changes were not observed in vivo following the HFD feeding. This finding supports the notion that, if female hypothalamic neurons experience a prolonged exposure to higher insulin levels, miR-1983 may be upregulated, but, as the female mice of both strains did not develop hyperinsulinemia within the timeframes analyzed, changes in miR-1983 levels were not observed. While there was a possibility that consumption of the HFD and other physiologic changes could alter miR-1983, this does not seem to be the case.

Further supporting the idea that in vivo changes in circulating insulin are required to alter hypothalamic miR-1983, treatment of mHypoE-46 cells with the most abundant saturated fatty acid comprising the HFD, palmitate at 50 µM for 24 hours, was found to cause a significant decrease in miR-1983 levels, opposite to that observed with insulin. This finding also agrees with previous data using a similar Npy/AgRP neuronal cell model, where it was determined that palmitate induces insulin resistance through alternate mechanisms compared to insulin (Mayer and Belsham, 2010b). This could have implications in obesity- and HFD-related T2DM versus the obesity-independent, hyperinsulinemic development of the disease in both lean and overweight humans.

Consumption of a HFD by the female mice of both C57Bl/6 and CD-1 backgrounds resulted in both a significant weight gain and fasting blood glucose levels. While it is generally accepted that female mice do not become insulin resistant in the periphery until much longer periods of time on a HFD diet (Medrikova et al., 2012), it was surprising to observe such parallel changes in the mRNA levels of major neuropeptides Npy, AgRP and Pomc as in the male mice within the timeframe of the study. This finding implies that while the majority of studies that use a HFD in their research exclude female mice because they do not display the expected peripheral changes as early as males do, it is possible that at the level of the brain they may in fact have significant alterations in neuropeptide content, thus should be examined in parallel to their male counterparts in metabolic studies.

Changes in miR-1983 appear before dysregulation of the neuropeptide levels in CD-1 male mice and disappear when the mice are left for 10 weeks on a HFD. This in vivo data is in agreement with the in vitro observations that miR-1983 is elevated after 24 hours, but not after 48 hours. A previous study detected a near significant 3-fold decrease in miR-1983, among a number of other miRNAs, in C57Bl/6 mice when placed on a restorative low fat diet after 8 weeks on a 58% HFD, but did not observe an increase in miR-1983 after 12 weeks in their HFD group (Hsieh et al., 2015). The impact of timing on miRNA expression in the hypothalamus has also been previously shown in rats fed a 45% HFD for 2 weeks and subsequent examination of miRNA levels after one and three months revealed differential effects on each miRNA species examined (Sangiao-Alvarellos et al., 2014).

REFERENCES

Agarwal, V., Bell, G. W., Nam, J. W., and Bartel, D. P. (2015). Predicting effective microRNA target sites in mammalian mRNAs. eLife 4.

Arroyo, J. D., Chevillet, J. R., Kroh, E. M., Ruf, I. K., Pritchard, C. C., Gibson, D. F., Mitchell, P. S., Bennett, C. F., Pogosova-Agadjanyan, E. L., Stirewalt, D. L., et al. (2011). Argonaute2 complexes carry a population of circulating microRNAs independent of vesicles in human plasma. Proceedings of the National Academy of Sciences of the United States of America 108, 5003-5008.

Balcells, Ingrid, Susanna Cirera, and Peter K Busk. "Specific and Sensitive Quantitative RT-PCR of miRNAs with DNA Primers." BMC Biotechnology 11 (2011): 70. PMC. Web. 24 Jul. 2018.

Belgardt, B. F., Okamura, T., and Bruning, J. C. (2009). Hormone and glucose signalling in POMC and AgRP neurons. The Journal of physiology 587, 5305-5314.

Belsham, D. D., Cai, F., Cui, H., Smukler, S. R., Salapatek, A. M., and Shkreta, L. (2004). Generation of a phenotypic array of hypothalamic neuronal cell models to study complex neuroendocrine disorders. Endocrinology 145, 393-400.

Bergen, H. T., Mizuno, T., Taylor, J., and Mobbs, C. V. (1999). Resistance to diet-induced obesity is associated with increased proopiomelanocortin mRNA and decreased neuropeptide Y mRNA in the hypothalamus. Brain research 851, 198-203.

Betel, D., Koppal, A., Agius, P., Sander, C., and Leslie, C. (2010). Comprehensive modeling of microRNA targets predicts functional non-conserved and non-canonical sites. Genome biology 11, R90.

Betel, D., Wilson, M., Gabow, A., Marks, D. S., and Sander, C. (2008). The microRNA.orq resource: targets and expression. Nucleic acids research 36, D149-153.

Bhattacharyya, S. N., Habermacher, R., Martine, U., Closs, E. I., and Filipowicz, W. (2006). Relief of microRNA-mediated translational repression in human cells subjected to stress. Cell 125, 1111-1124.

Born, J., Lange, T., Kern, W., McGregor, G. P., Bickel, U., and Fehm, H. L. (2002). Sniffing neuropeptides: a transnasal approach to the human brain. Nature neuroscience 5, 514-516. Bruning, J. C., Gautam, D., Burks, D. J., Gillette, J., Schubert, M., Orban, P. C., Klein, R., Krone, W., Muller-Wieland, D., and Kahn, C. R. (2000). Role of brain insulin receptor in control of body weight and reproduction. Science 289, 2122-2125.

Clegg, D. J., Gotoh, K., Kemp, C., Wortman, M. D., Benoit, S. C., Brown, L. M., D'Alessio, D., Tso, P., Seeley, R. J., and Woods, S. C. (2011). Consumption of a high-fat diet induces central insulin resistance independent of adiposity. Physiology & behavior 103, 10-16.

Crepin, D., Benomar, Y., Riffault, L., Amine, H., Gertler, A., and Taouis, M. (2014). The over-expression of miR-200a in the hypothalamus of ob/ob mice is linked to leptin and insulin signaling impairment. Molecular and cellular endocrinology 384, 1-11.

Dhillon, S. S., McFadden, S. A., Chalmers, J. A., Centeno, M. L., Kim, G. L., and Belsham, D. D. (2011). Cellular leptin resistance impairs the leptin-mediated suppression of neuropeptide Y secretion in hypothalamic neurons. Endocrinology 152, 4138-4147.

Dhuria, S. V., Hanson, L. R., and Frey, W. H., 2nd (2010). Intranasal delivery to the central nervous system: mechanisms and experimental considerations. Journal of pharmaceutical sciences 99, 1654-1673.

Dweep, H., and Gretz, N. (2015). miRWalk2.0: a comprehensive atlas of microRNA-target interactions. Nature methods 12, 697.

Dweep, H., Sticht, C., Pandey, P., and Gretz, N. (2011). miRWalk-database: prediction of possible miRNA binding sites by "walking" the genes of three genomes. Journal of biomedical informatics 44, 839-847.

Edinger, R. S., Coronnello, C., Bodnar, A. J., Labarca, M., Bhalla, V., LaFramboise, W. A., Benos, P. V., Ho, J., Johnson, J. P., and Butterworth, M. B. (2014). Aldosterone regulates microRNAs in the cortical collecting duct to alter sodium transport. Journal of the American Society of Nephrology: JASN 25, 2445-2457.

Feng, J., Xing, W., and Xie, L. (2016). Regulatory Roles of MicroRNAs in Diabetes. International journal of molecular sciences 17.

Gao, Q., and Horvath, T. L. (2008). Neuronal control of energy homeostasis. FEBS letters 582, 132-141.

Hashimoto, N., and Tanaka, T. (2016). Role of miRNAs in the pathogenesis and susceptibility of diabetes mellitus. Journal of human genetics.

Hasler, D., Lehmann, G., Murakawa, Y., Klironomos, F., Jakob, L., Grasser, F. A., Rajewsky, N., Landthaler, M., and Meister, G. (2016). The Lupus Autoantigen La Prevents Mis-channeling of tRNA Fragments into the Human MicroRNA Pathway. Molecular cell 63, 110124.

Herzer, S., Silahtaroglu, A., and Meister, B. (2012). Locked nucleic acid-based in situ hybridisation reveals miR-7a as a hypothalamus-enriched microRNA with a distinct expression pattern. Journal of neuroendocrinology 24, 1492-1504.

Hollander, J. A., Im, H. I., Amelio, A. L., Kocerha, J., Bali, P., Lu, Q., Willoughby, D., Wahlestedt, C., Conkright, M. D., and Kenny, P. J. (2010). Striatal microRNA controls cocaine intake through CREB signalling. Nature 466, 197-202.

Hsieh, C. H., Rau, C. S., Wu, S. C., Yang, J. C., Wu, Y. C., Lu, T. H., Tzeng, S. L., Wu, C. J., and Lin, C. W. (2015). Weight-reduction through a low-fat diet causes differential expression of circulating microRNAs in obese C57BL/6 mice. BMC genomics 16, 699.

Janssen, H. L., Reesink, H. W., Lawitz, E. J., Zeuzem, S., Rodriguez-Torres, M., Patel, K., van der Meer, A. J., Patick, A. K., Chen, A., Zhou, Y., et al. (2013). Treatment of HCV infection by targeting microRNA. The New England journal of medicine 368, 1685-1694.

Kaushik, S., Arias, E., Kwon, H., Lopez, N. M., Athonvarangkul, D., Sahu, S., Schwartz, G. J., Pessin, J. E., and Singh, R. (2012). Loss of autophagy in hypothalamic POMC neurons impairs lipolysis. EMBO reports 13, 258-265.

Kim, J. M., Lee, S. T., Chu, K., Jung, K. H., Kim, J. H., Yu, J. S., Kim, S., Kim, S. H., Park, D. K., Moon, J., et al. (2014). Inhibition of Let7c microRNA is neuroprotective in a rat intracerebral hemorrhage model. PloS one 9, e97946.

Kleinridders, A., Ferris, H. A., Cai, W., and Kahn, C. R. (2014). Insulin action in brain regulates systemic metabolism and brain function. Diabetes 63, 2232-2243.

Konner, A. C., and Bruning, J. C. (2012). Selective insulin and leptin resistance in metabolic disorders. Cell metabolism 16, 144-152.

Kornfeld, J. W., Baitzel, C., Konner, A. C., Nicholls, H. T., Vogt, M. C., Herrmanns, K., Scheja, L., Haumaitre, C., Wolf, A. M., Knippschild, U., et al. (2013). Obesity-induced overexpression of miR-802 impairs glucose metabolism through silencing of Hnf1b. Nature 494, 111-115.

Kuehnert, J. et al. Novel RNA chaperone domain of RNA-binding protein La is regulated by AKT phosphorylation. Nucleic acids research 43, 581-594, doi:10.1093/nar/gku1309 (2015).

Lee, A. K., Mojtahed-Jaberi, M., Kyriakou, T., Astarloa, E. A., Arno, M., Marshall, N. J., Brain, S. D., and O'Dell, S. D. (2010). Effect of high-fat feeding on expression of genes controlling availability of dopamine in mouse hypothalamus. Nutrition 26, 411-422.

Lee, S. T., Chu, K., Jung, K. H., Kim, J. H., Huh, J. Y., Yoon, H., Park, D. K., Lim, J. Y., Kim, J. M., Jeon, D., et al. (2012). miR-206 regulates brain-derived neurotrophic factor in Alzheimer disease model. Annals of neurology 72, 269-277.

Levy, J. C., Matthews, D. R. & Hermans, M. P. Correct homeostasis model assessment (HOMA) evaluation uses the computer program. *Diabetes* care 21, 2191-2192 (1998).

Lewis, B. P., Burge, C. B., and Bartel, D. P. (2005). Conserved seed pairing, often flanked by adenosines, indicates that thousands of human genes are microRNA targets. Cell 120, 1520.

Li, Y., and Kowdley, K. V. (2012). Method for microRNA isolation from clinical serum samples. Analytical biochemistry 431, 69-75.

Liu, J., Valencia-Sanchez, M. A., Hannon, G. J., and Parker, R. (2005). MicroRNA-dependent localization of targeted mRNAs to mammalian P-bodies. Nature cell biology 7, 719-723.

Liu, Y., Prentice, K. J., Eversley, J. A., Hu, C., Batchuluun, B., Leavey, K., Hansen, J. B., Wei, D. W., Cox, B., Dai, F. F., et al. (2016). Rapid Elevation in CMPF May Act As a Tipping Point in Diabetes Development. Cell reports 14, 2889-2900.

Livak, K. J., and Schmittgen, T. D. (2001). Analysis of relative gene expression data using real-time quantitative PCR and the 2(-Delta Delta C(T)) Method. Methods 25, 402-408. Mayer, C. M., and Belsham, D. D. (2009). Insulin directly regulates NPY and AgRP gene expression via the MAPK MEK/ERK signal transduction pathway in mHypoE-46 hypothalamic neurons. Molecular and cellular endocrinology 307, 99-108.

Loh, K. et al. Insulin controls food intake and energy balance via NPY neurons. *Molecular metabolism* 6, 574-584, doi:10.1016/j.molmet.2017.03.013 (2017).

Mayer, C. M., and Belsham, D. D. (2010a). Central insulin signaling is attenuated by long-term insulin exposure via insulin receptor substrate-1 serine phosphorylation, proteasomal degradation, and lysosomal insulin receptor degradation. Endocrinology 151, 75-84.

Mayer, C. M., and Belsham, D. D. (2010b). Palmitate attenuates insulin signaling and induces endoplasmic reticulum stress and apoptosis in hypothalamic neurons: rescue of resistance and apoptosis through adenosine 5' monophosphate-activated protein kinase activation. Endocrinology 151, 576-585.

Medrikova, D., Jilkova, Z. M., Bardova, K., Janovska, P., Rossmeisl, M., and Kopecky, J. (2012). Sex differences during the course of diet-induced obesity in mice: adipose tissue expandability and glycemic control. International journal of obesity 36, 262-272.

Meister, B., Herzer, S., and Silahtaroglu, A. (2013). MicroRNAs in the hypothalamus. Neuroendocrinology 98, 243-253.

Meredith, M. E., Salameh, T. S., and Banks, W. A. (2015). Intranasal Delivery of Proteins and Peptides in the Treatment of Neurodegenerative Diseases. AAPS J 17, 780-787.

Mi, H., Muruganujan, A., Casagrande, J. T., and Thomas, P. D. (2013). Large-scale gene function analysis with the PANTHER classification system. Nature protocols 8, 1551-1566. Mi, H., Poudel, S., Muruganujan, A., Casagrande, J. T., and Thomas, P. D. (2016). PANTHER version 10: expanded protein families and functions, and analysis tools. Nucleic acids research 44, D336-342.

Miranda, K. C., Huynh, T., Tay, Y., Ang, Y. S., Tam, W. L., Thomson, A. M., Lim, B., and Rigoutsos, I. (2006). A pattern-based method for the identification of MicroRNA binding sites and their corresponding heteroduplexes. Cell 126, 1203-1217.

Nazarians-Armavil, A., Chalmers, J. A., Lee, C. B., Ye, W., and Belsham, D. D. (2014). Cellular insulin resistance disrupts hypothalamic mHypoA-POMC/GFP neuronal signaling pathways. The Journal of endocrinology 220, 13-24.

Obici, S., Feng, Z., Karkanias, G., Baskin, D. G., and Rossetti, L. (2002a). Decreasing hypothalamic insulin receptors causes hyperphagia and insulin resistance in rats. Nature neuroscience 5, 566-572.

Obici, S., Zhang, B. B., Karkanias, G., and Rossetti, L. (2002b). Hypothalamic insulin signaling is required for inhibition of glucose production. Nature medicine 8, 1376-1382.

Parrizas, M., and Novials, A. (2016). Circulating microRNAs as biomarkers for metabolic disease. Best practice & research. Clinical endocrinology & metabolism 30, 591-601.

Prentice, K. J., Luu, L., Allister, E. M., Liu, Y., Jun, L. S., Sloop, K. W., Hardy, A. B., Wei, L., Jia, W., Fantus, I. G., et al. (2014). The furan fatty acid metabolite CMPF is elevated in diabetes and induces beta cell dysfunction. Cell metabolism 19, 653-666.

Rizza, R. A., Mandarino, L. J., Genest, J., Baker, B. A., and Gerich, J. E. (1985). Production of insulin resistance by hyperinsulinaemia in man. Diabetologia 28, 70-75.

Roh, E., Song do, K., and Kim, M. S. (2016). Emerging role of the brain in the homeostatic regulation of energy and glucose metabolism. Experimental & molecular medicine 48, e216.

Sangiao-Alvarellos, S., Pena-Bello, L., Manfredi-Lozano, M., Tena-Sempere, M., and Cordido, F. (2014). Perturbation of hypothalamic microRNA expression patterns in male rats after metabolic distress: impact of obesity and conditions of negative energy balance. Endocrinology 155, 1838-1850.

Scherer, T., O'Hare, J., Diggs-Andrews, K., Schweiger, M., Cheng, B., Lindtner, C., Zielinski, E., Vempati, P., Su, K., Dighe, S., et al. (2011). Brain insulin controls adipose tissue lipolysis and lipogenesis. Cell metabolism 13, 183-194.

Seeger, T., Fischer, A., Muhly-Reinholz, M., Zeiher, A. M., and Dimmeler, S. (2014). Long-term inhibition of miR-21 leads to reduction of obesity in db/db mice. Obesity 22, 2352-2360.

Thaler, J. P., Yi, C. X., Schur, E. A., Guyenet, S. J., Hwang, B. H., Dietrich, M. O., Zhao, X., Sarruf, D. A., Izgur, V., Maravilla, K. R., et al. (2012). Obesity is associated with hypothalamic injury in rodents and humans. The Journal of clinical investigation 122, 153-162.

Trajkovski, M., Hausser, J., Soutschek, J., Bhat, B., Akin, A., Zavolan, M., Heim, M. H., and Stoffel, M. (2011). MicroRNAs 103 and 107 regulate insulin sensitivity. Nature 474, 649-653.

Turchinovich, A., Weiz, L., Langheinz, A., and Burwinkel, B. (2011). Characterization of extracellular circulating microRNA. Nucleic acids research 39, 7223-7233.

Valadi, H., Ekstrom, K., Bossios, A., Sjostrand, M., Lee, J. J., and Lotvall, J. O. (2007). Exosome-mediated transfer of mRNAs and microRNAs is a novel mechanism of genetic exchange between cells. Nature cell biology 9, 654-659.

Varela, L., and Horvath, T. L. (2012). Leptin and insulin pathways in POMC and AgRP neurons that modulate energy balance and glucose homeostasis. EMBO reports 13, 10791086.

Vienberg, S., Geiger, J., Madsen, S., and Dalgaard, L. T. (2016). MicroRNAs in Metabolism. Acta physiologica.

Vinnikov, I. A., Hajdukiewicz, K., Reymann, J., Beneke, J., Czajkowski, R., Roth, L. C., Novak, M., Roller, A., Dorner, N., Starkuviene, V., et al. (2014). Hypothalamic miR-103 protects from hyperphagic obesity in mice. The Journal of neuroscience: the official journal of the Society for Neuroscience 34, 10659-10674.

Wellhauser, L., Chalmers, J. A., and Belsham, D. D. (2016). Nitric Oxide Exerts Basal and Insulin-Dependent Anorexigenic Actions in POMC Hypothalamic Neurons. Molecular endocrinology 30, 402-416.

The invention claimed is:

1. A miR-1983 inhibitor that comprises an anti-miR-1983 oligonucleotide consisting of a nucleotide sequence selected from nucleotides 9 to 15, 8 to 15, 7 to 15, 6 to 15, 5 to 15, 4 to 15, 3 to 15, 2 to 15 or 1 to 15 of 5'-3', A*C*A*T/U*G*C*T/U*C*C*A*G*G*T/U*G*A (SEQ ID NO: 2).

2. The miR-1983 inhibitor of claim 1, wherein the anti-miR-1983 oligonucleotide comprises RNA.

3. The miR-1983 inhibitor of claim 1, wherein the anti-miR-1983 oligonucleotide is chemically modified.

4. The miR-1983 inhibitor of claim 3, wherein the chemically modified anti-miR-1983 oligonucleotide comprises a chemical modification at a 2' position.

5. The miR-1983 inhibitor of claim 4, wherein the chemical modification is selected from the group consisting of 2'-O-methyl (2': 0-Me), 2'-O-methoxyethyl (2'O-MOE), 2'-fluoro (2'$_2$F), and locked nucleic acid monomer (LNAM).

6. The miR-1983 inhibitor of claim 5, wherein the anti-miR-1983 oligonucleotide comprises a plurality of chemically modified nucleotide monomers.

7. The miR-1983 inhibitor of claim 6, wherein the anti-miR-1983 oligonucleotide comprises a plurality of LNAMs.

8. The miR-1983 inhibitor of claim 7, wherein the anti-miR-1983 oligonucleotide is a locked nucleic acid (LNA) or a LNA/DNA mixmer.

9. The miR-1983 inhibitor of claim 8, wherein the LNA comprises sequence 5'-3', A*C*A*T/U*G*C*T/U*C*C*A*G*G*T/U*G*A (SEQ ID NO: 2).

10. The miR-1983 inhibitor of claim 9, wherein the LNA comprises sequence 5'-3', A*C*A*T*G*C*T*C*C*A*G*G*T*G*A (SEQ ID NO: 2).

11. The miR-1983 inhibitor of claim 9, wherein the LNA comprises sequence 5'-3', A*C*A*U*G*C*U*C*C*A*G*G*U*G*A (SEQ ID NO: 2).

12. The miR-1983 inhibitor of claim 1, wherein the anti-miR-1983 oligonucleotide comprises at least one mismatch and up to 4 mismatches.

13. The miR-1983 inhibitor of claim 1, wherein the anti-miR-1983 oligonucleotide is double stranded.

14. The miR-1983 inhibitor of claim 1, wherein the anti-miR-1983 oligonucleotide is single stranded.

15. The miR-1983 inhibitor of claim 1, wherein the miR-1983 inhibitor consists of the anti-miR-1983 oligonucleotide.

16. A composition comprising the miR-1983 inhibitor of claim 1 and a diluent.

17. The composition of claim 16 formulated as an intranasal formulation.

18. The composition of claim 16, wherein the diluent comprises saline.

19. A method of improving insulin sensitivity in a subject, the method comprising administering a miR-1983 inhibitor to a subject in need thereof.

20. The method of claim 19 wherein the miR-1983 inhibitor comprises an anti-miR-1983 oligonucleotide that is complementary to at least part of CTCACCTGGAGCATGTTTTCT (SEQ ID NO: 1), the part comprising at least nucleotides 2 to 8 of CTCACCTGGAGCATGTTTTCT (SEQ ID NO: 1) or a composition comprising said inhibitor.

21. The method of claim 19 wherein the miR-1983 inhibitor is administered intranasally.

* * * * *

SEQUENCE LISTING

```
<160> NUMBER OF SEQ ID NOS: 39

<210> SEQ ID NO 1
<211> LENGTH: 21
<212> TYPE: DNA
<213> ORGANISM: Homo Sapiens
<220> FEATURE:
<221> NAME/KEY: misc_feature
<222> LOCATION: (2)..(2)
<223> OTHER INFORMATION: n is t or u
<220> FEATURE:
<221> NAME/KEY: misc_feature
<222> LOCATION: (7)..(7)
<223> OTHER INFORMATION: n is t or u
<220> FEATURE:
<221> NAME/KEY: misc_feature
<222> LOCATION: (14)..(14)
<223> OTHER INFORMATION: n is t or u
<220> FEATURE:
<221> NAME/KEY: misc_feature
<222> LOCATION: (16)..(19)
<223> OTHER INFORMATION: n is t or u
<220> FEATURE:
<221> NAME/KEY: misc_feature
<222> LOCATION: (21)..(21)
<223> OTHER INFORMATION: n is t or u

<400> SEQUENCE: 1
cncaccngga gcangnnnnc n                                              21

<210> SEQ ID NO 2
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: n is t or u
<220> FEATURE:
<221> NAME/KEY: misc_feature
<222> LOCATION: (7)..(7)
<223> OTHER INFORMATION: n is t or u
<220> FEATURE:
<221> NAME/KEY: misc_feature
```

```
<222> LOCATION: (13)..(13)
<223> OTHER INFORMATION: n is t or u

<400> SEQUENCE: 2
acangcncca ggnga                                                    15

<210> SEQ ID NO 3
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: n is t or u
<220> FEATURE:
<221> NAME/KEY: misc_feature
<222> LOCATION: (6)..(6)
<223> OTHER INFORMATION: n is t or u
<220> FEATURE:
<221> NAME/KEY: misc_feature
<222> LOCATION: (8)..(8)
<223> OTHER INFORMATION: n is t or u

<400> SEQUENCE: 3
acgncnanac gccca                                                    15

<210> SEQ ID NO 4
<211> LENGTH: 15
<212> TYPE: DNA
<213> ORGANISM: Homo Sapiens
<220> FEATURE:
<221> NAME/KEY: misc_feature
<222> LOCATION: (1)..(1)
<223> OTHER INFORMATION: n is t or u
<220> FEATURE:
<221> NAME/KEY: misc_feature
<222> LOCATION: (6)..(6)
<223> OTHER INFORMATION: n is t or u
<220> FEATURE:
<221> NAME/KEY: misc_feature
<222> LOCATION: (13)..(13)
<223> OTHER INFORMATION: n is t or u
<220> FEATURE:
<221> NAME/KEY: misc_feature
<222> LOCATION: (15)..(15)
<223> OTHER INFORMATION: n is t or u

<400> SEQUENCE: 4
ncaccnggag cangn                                                    15

<210> SEQ ID NO 5
<211> LENGTH: 14
<212> TYPE: DNA
<213> ORGANISM: Homo Sapiens
<220> FEATURE:
<221> NAME/KEY: misc_feature
<222> LOCATION: (1)..(1)
<223> OTHER INFORMATION: n is t or u
<220> FEATURE:
<221> NAME/KEY: misc_feature
<222> LOCATION: (6)..(6)
<223> OTHER INFORMATION: n is t or u
<220> FEATURE:
<221> NAME/KEY: misc_feature
<222> LOCATION: (13)..(13)
<223> OTHER INFORMATION: n is t or u

<400> SEQUENCE: 5
ncaccnggag cang                                                     14
```

```
<210> SEQ ID NO 6
<211> LENGTH: 13
<212> TYPE: DNA
<213> ORGANISM: Homo Sapiens
<220> FEATURE:
<221> NAME/KEY: misc_feature
<222> LOCATION: (1)..(1)
<223> OTHER INFORMATION: n is t or u
<220> FEATURE:
<221> NAME/KEY: misc_feature
<222> LOCATION: (6)..(6)
<223> OTHER INFORMATION: n is t or u
<220> FEATURE:
<221> NAME/KEY: misc_feature
<222> LOCATION: (13)..(13)
<223> OTHER INFORMATION: n is t or u

<400> SEQUENCE: 6
ncaccnggag can                                                          13

<210> SEQ ID NO 7
<211> LENGTH: 12
<212> TYPE: DNA
<213> ORGANISM: Homo Sapiens
<220> FEATURE:
<221> NAME/KEY: misc_feature
<222> LOCATION: (1)..(1)
<223> OTHER INFORMATION: n is t or u
<220> FEATURE:
<221> NAME/KEY: misc_feature
<222> LOCATION: (6)..(6)
<223> OTHER INFORMATION: n is t or u

<400> SEQUENCE: 7
ncaccnggag ca                                                           12

<210> SEQ ID NO 8
<211> LENGTH: 11
<212> TYPE: DNA
<213> ORGANISM: Homo Sapiens
<220> FEATURE:
<221> NAME/KEY: misc_feature
<222> LOCATION: (1)..(1)
<223> OTHER INFORMATION: n is t or u
<220> FEATURE:
<221> NAME/KEY: misc_feature
<222> LOCATION: (6)..(6)
<223> OTHER INFORMATION: n is t or u

<400> SEQUENCE: 8
ncaccnggag c                                                            11

<210> SEQ ID NO 9
<211> LENGTH: 10
<212> TYPE: DNA
<213> ORGANISM: Homo Sapiens
<220> FEATURE:
<221> NAME/KEY: misc_feature
<222> LOCATION: (1)..(1)
<223> OTHER INFORMATION: n is t or u
<220> FEATURE:
<221> NAME/KEY: misc_feature
<222> LOCATION: (6)..(6)
<223> OTHER INFORMATION: n is t or u

<400> SEQUENCE: 9 ncaccnggag                                                              10

<210> SEQ ID NO 10
<211> LENGTH: 9
```

```
<212> TYPE: DNA
<213> ORGANISM: Homo Sapiens
<220> FEATURE:
<221> NAME/KEY: misc_feature
<222> LOCATION: (1)..(1)
<223> OTHER INFORMATION: n is t or u
<220> FEATURE:
<221> NAME/KEY: misc_feature
<222> LOCATION: (6)..(6)
<223> OTHER INFORMATION: n is t or u

<400> SEQUENCE: 10 ncaccngga                                                                     9

<210> SEQ ID NO 11
<211> LENGTH: 8
<212> TYPE: DNA
<213> ORGANISM: Homo Sapiens
<220> FEATURE:
<221> NAME/KEY: misc_feature
<222> LOCATION: (1)..(1)
<223> OTHER INFORMATION: n is t or u
<220> FEATURE:
<221> NAME/KEY: misc_feature
<222> LOCATION: (6)..(6)
<223> OTHER INFORMATION: n is t or u

<400> SEQUENCE: 11 ncaccngg                                                                      8

<210> SEQ ID NO 12
<211> LENGTH: 7
<212> TYPE: DNA
<213> ORGANISM: Homo Sapiens
<220> FEATURE:
<221> NAME/KEY: misc_feature
<222> LOCATION: (1)..(1)
<223> OTHER INFORMATION: n is t or u
<220> FEATURE:
<221> NAME/KEY: misc_feature
<222> LOCATION: (6)..(6)
<223> OTHER INFORMATION: n is t or u

<400> SEQUENCE: 12 ncaccng                                                                       7

<210> SEQ ID NO 13
<211> LENGTH: 16
<212> TYPE: DNA
<213> ORGANISM: Homo Sapiens
<220> FEATURE:
<221> NAME/KEY: misc_feature
<222> LOCATION: (2)..(2)
<223> OTHER INFORMATION: n is t or u
<220> FEATURE:
<221> NAME/KEY: misc_feature
<222> LOCATION: (7)..(7)
<223> OTHER INFORMATION: n is t or u
<220> FEATURE:
<221> NAME/KEY: misc_feature
<222> LOCATION: (14)..(14)
<223> OTHER INFORMATION: n is t or u
<220> FEATURE:
<221> NAME/KEY: misc_feature
<222> LOCATION: (16)..(16)
<223> OTHER INFORMATION: n is t or u

<400> SEQUENCE: 13
cncaccngga gcangn                                                            16

<210> SEQ ID NO 14
```

-continued

```
<211> LENGTH: 15
<212> TYPE: DNA
<213> ORGANISM: Homo Sapiens
<220> FEATURE:
<221> NAME/KEY: misc_feature
<222> LOCATION: (2)..(2)
<223> OTHER INFORMATION: n is t or u
<220> FEATURE:
<221> NAME/KEY: misc_feature
<222> LOCATION: (7)..(7)
<223> OTHER INFORMATION: n is t or u
<220> FEATURE:
<221> NAME/KEY: misc_feature
<222> LOCATION: (14)..(14)
<223> OTHER INFORMATION: n is t or u

<400> SEQUENCE: 14
cncaccngga gcang                                                    15

<210> SEQ ID NO 15
<211> LENGTH: 14
<212> TYPE: DNA
<213> ORGANISM: Homo Sapiens
<220> FEATURE:
<221> NAME/KEY: misc_feature
<222> LOCATION: (2)..(2)
<223> OTHER INFORMATION: n is t or u
<220> FEATURE:
<221> NAME/KEY: misc_feature
<222> LOCATION: (7)..(7)
<223> OTHER INFORMATION: n is t or u
<220> FEATURE:
<221> NAME/KEY: misc_feature
<222> LOCATION: (14)..(14)
<223> OTHER INFORMATION: n is t or u

<400> SEQUENCE: 15
cncaccngga gcan                                                     14

<210> SEQ ID NO 16
<211> LENGTH: 13
<212> TYPE: DNA
<213> ORGANISM: Homo Sapiens
<220> FEATURE:
<221> NAME/KEY: misc_feature
<222> LOCATION: (2)..(2)
<223> OTHER INFORMATION: n is t or u
<220> FEATURE:
<221> NAME/KEY: misc_feature
<222> LOCATION: (7)..(7)
<223> OTHER INFORMATION: n is t or u

<400> SEQUENCE: 16
cncaccngga gca                                                      13

<210> SEQ ID NO 17
<211> LENGTH: 12
<212> TYPE: DNA
<213> ORGANISM: Homo Sapiens
<220> FEATURE:
<221> NAME/KEY: misc_feature
<222> LOCATION: (2)..(2)
<223> OTHER INFORMATION: n is t or u
<220> FEATURE:
<221> NAME/KEY: misc_feature
<222> LOCATION: (7)..(7)
<223> OTHER INFORMATION: n is t or u

<400> SEQUENCE: 17
cncaccngga gc                                                       12
```

```
<210> SEQ ID NO 18
<211> LENGTH: 11
<212> TYPE: DNA
<213> ORGANISM: Homo Sapiens
<220> FEATURE:
<221> NAME/KEY: misc_feature
<222> LOCATION: (2)..(2)
<223> OTHER INFORMATION: n is t or u
<220> FEATURE:
<221> NAME/KEY: misc_feature
<222> LOCATION: (7)..(7)
<223> OTHER INFORMATION: n is t or u

<400> SEQUENCE: 18
cncaccngga g                                                           11

<210> SEQ ID NO 19
<211> LENGTH: 10
<212> TYPE: DNA
<213> ORGANISM: Homo Sapiens
<220> FEATURE:
<221> NAME/KEY: misc_feature
<222> LOCATION: (2)..(2)
<223> OTHER INFORMATION: n is t or u
<220> FEATURE:
<221> NAME/KEY: misc_feature
<222> LOCATION: (7)..(7)
<223> OTHER INFORMATION: n is t or u

<400> SEQUENCE: 19 cncaccngga                                                             10

<210> SEQ ID NO 20
<211> LENGTH: 9
<212> TYPE: DNA
<213> ORGANISM: Homo Sapiens
<220> FEATURE:
<221> NAME/KEY: misc_feature
<222> LOCATION: (2)..(2)
<223> OTHER INFORMATION: n is t or u
<220> FEATURE:
<221> NAME/KEY: misc_feature
<222> LOCATION: (7)..(7)
<223> OTHER INFORMATION: n is t or u

<400> SEQUENCE: 20 cncaccngg                                                               9

<210> SEQ ID NO 21
<211> LENGTH: 8
<212> TYPE: DNA
<213> ORGANISM: Homo Sapiens
<220> FEATURE:
<221> NAME/KEY: misc_feature
<222> LOCATION: (2)..(2)
<223> OTHER INFORMATION: n is t or u
<220> FEATURE:
<221> NAME/KEY: misc_feature
<222> LOCATION: (7)..(7)
<223> OTHER INFORMATION: n is t or u

<400> SEQUENCE: 21 cncaccng                                                                8

<210> SEQ ID NO 22
<211> LENGTH: 21
<212> TYPE: DNA
<213> ORGANISM: Mus Musculus

<400> SEQUENCE: 22
```
cggaggtgct agatccacag a                                              21

<210> SEQ ID NO 23
<211> LENGTH: 21
<212> TYPE: DNA
<213> ORGANISM: Mus Musculus

<400> SEQUENCE: 23
aggactcgtg cagccttaca c                                              21

<210> SEQ ID NO 24
<211> LENGTH: 21
<212> TYPE: DNA
<213> ORGANISM: Mus Musculus

<400> SEQUENCE: 24
cgcttccaga gtgcagctat t                                              21

<210> SEQ ID NO 25
<211> LENGTH: 23
<212> TYPE: DNA
<213> ORGANISM: Mus Musculus

<400> SEQUENCE: 25
atcttcaaaa aggccaacca gat                                            23

<210> SEQ ID NO 26
<211> LENGTH: 23
<212> TYPE: DNA
<213> ORGANISM: Mus Musculus

<400> SEQUENCE: 26
tcccatcaaa tattgccaaa att                                            23

<210> SEQ ID NO 27
<211> LENGTH: 27
<212> TYPE: DNA
<213> ORGANISM: Mus Musculus

<400> SEQUENCE: 27
cagaaataga taaatacttc caatcac                                        27

<210> SEQ ID NO 28
<211> LENGTH: 18
<212> TYPE: DNA
<213> ORGANISM: Mus Musculus

<400> SEQUENCE: 28 cagaaacgc ccccagaa                                                   18

<210> SEQ ID NO 29
<211> LENGTH: 25
<212> TYPE: DNA
<213> ORGANISM: Mus Musculus

<400> SEQUENCE: 29
aaaagtcggg agaacaagtt tcatt                                          25

<210> SEQ ID NO 30
<211> LENGTH: 20
<212> TYPE: DNA
<213> ORGANISM: Mus Musculus

<400> SEQUENCE: 30
cccgcccaag gacaagcgtt                                               20

<210> SEQ ID NO 31
<211> LENGTH: 20
<212> TYPE: DNA
<213> ORGANISM: Mus Musculus

<400> SEQUENCE: 31
ctggcccttc ttgtgcgcgt                                               20

<210> SEQ ID NO 32
<211> LENGTH: 36
<212> TYPE: DNA
<213> ORGANISM: Artificial Sequence
<220> FEATURE:
<223> OTHER INFORMATION: Synthetic

<400> SEQUENCE: 32
ttgtctgcat gagctctcag aagtcttgct caggtg                             36

<210> SEQ ID NO 33
<211> LENGTH: 37
<212> TYPE: DNA
<213> ORGANISM: Artificial Sequence
<220> FEATURE:
<223> OTHER INFORMATION: Synthetic

<400> SEQUENCE: 33
cggtctgacc cgtcgacacc atcattcatt taccaag                            37

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
gatcgccgtg taattctagt                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
atgttgccag ggaactcaat                                               20

<210> SEQ ID NO 36
<211> LENGTH: 20
<212> TYPE: DNA
<213> ORGANISM: Mus Musculus

<400> SEQUENCE: 36
ccaactcagc ttcctttcgg                                               20

<210> SEQ ID NO 37
<211> LENGTH: 22
<212> TYPE: RNA
<213> ORGANISM: Caenorhabditis elegans

<400> SEQUENCE: 37

```
ucaccgggug uaaaucagcu ug                                          22

<210> SEQ ID NO 38
<211> LENGTH: 23
<212> TYPE: RNA
<213> ORGANISM: Mus musculus

<400> SEQUENCE: 38
aaggagaaau aaaaacaggu gag                                         23

<210> SEQ ID NO 39
<211> LENGTH: 21
<212> TYPE: RNA
<213> ORGANISM: Artificial Sequence
<220> FEATURE:
<223> OTHER INFORMATION: Synthetic Construct

<400> SEQUENCE: 39
ucuuuuguac gagguccacu c                                           21
```